United States Patent
Anderson et al.

(10) Patent No.: US 8,439,816 B2
(45) Date of Patent: May 14, 2013

(54) PIEZOELECTRIC, MICRO-EXERCISE APPARATUS AND METHOD

(75) Inventors: Gregory S. Anderson, Sandy, UT (US);
Kade E. Huntsman, Holladay, UT (US);
Dale C. Gledhill, Sandy, UT (US);
Douglas R. Burrell, Springville, UT (US); David Xiao, Hangzhou (CN)

(73) Assignee: Pulse, LLC, Draper, UT (US)

( * ) Notice: Subject to any disclaimer, the term of this patent is extended or adjusted under 35 U.S.C. 154(b) by 776 days.

(21) Appl. No.: 12/502,998

(22) Filed: Jul. 14, 2009

(65) Prior Publication Data

US 2011/0015555 A1    Jan. 20, 2011

(51) Int. Cl.
*A61N 2/04* (2006.01)

(52) U.S. Cl.
USPC .................................... 600/13; 600/9; 600/15

(58) Field of Classification Search ................ 600/9, 13, 600/14, 15; 128/897–899
See application file for complete search history.

(56) References Cited

U.S. PATENT DOCUMENTS

| | | | |
|---|---|---|---|
| 4,105,017 A | 8/1978 | Ryaby et al. | |
| 4,266,533 A | 5/1981 | Ryaby et al. | |
| 4,315,503 A | 2/1982 | Ryaby et al. | |
| 4,510,704 A * | 4/1985 | Johnson | 36/136 |
| 5,014,699 A | 5/1991 | Pollack et al. | |
| 5,058,582 A | 10/1991 | Thaler | |
| 5,087,336 A | 2/1992 | Liboff et al. | |
| 5,160,591 A | 11/1992 | Liboff et al. | |
| 5,181,902 A | 1/1993 | Erickson et al. | |
| 5,269,745 A | 12/1993 | Liboff et al. | |
| 5,269,747 A | 12/1993 | Erickson et al. | |
| 5,290,409 A | 3/1994 | Liboff et al. | |
| 5,338,286 A | 8/1994 | Abbott et al. | |
| 5,370,133 A * | 12/1994 | Darby et al. | 128/882 |
| 5,458,558 A * | 10/1995 | Liboff et al. | 600/13 |
| 5,654,694 A | 8/1997 | Newham | |
| 5,743,844 A | 4/1998 | Tepper et al. | |
| 5,792,209 A | 8/1998 | Varner | |
| 5,951,459 A * | 9/1999 | Blackwell | 600/13 |
| 5,997,464 A | 12/1999 | Blackwell | |
| 6,024,691 A | 2/2000 | Tepper et al. | |
| 6,132,362 A | 10/2000 | Tepper et al. | |

(Continued)

OTHER PUBLICATIONS

Daodaor Technologies Limited, "A New Idea on the Magnetic Products," 258 Zhonghe Zhong Road, Hangzhou, 310003, Phone: 86-571-86559319; 4 pages;, Rec May 4, 2010.
Advanced Biomagentics® Clinical Database: Osteoporosis Studies, therion®, http://www.therionresearch.com/database/osteoporosis.html#2, Nov. 11, 2006.

(Continued)

*Primary Examiner* — Charles A Marmor, II
*Assistant Examiner* — Joshua D Lannu
(74) *Attorney, Agent, or Firm* — Pate Baird, PLLC

(57) ABSTRACT

An apparatus and method for micro-exercise apply piezoelectric stress to cells of a bone mass by inducing voltages in the bone mass. Application of dynamic, electromagnetic fields passing through the conductive bone mass induce currents and voltages locally in and around cells or groups of cells. The cells respond to the combination of mechanical stress and strain by building themselves up as they would if they had been subjected to the stress and strain of conventional exercise. Thus, micro-exercise at a cellular level of the bone mass can be stimulated as if the stress and strain had been applied to the entire bone structure of which the smaller cellular portions are constituent parts. In combination with casts or splints, the sources of electromagnetic flux may be embedded in the frame or solid structure, the protective padding added for comfort, or both.

19 Claims, 41 Drawing Sheets

U.S. PATENT DOCUMENTS

| | | | |
|---|---|---|---|
| 6,174,276 B1 | 1/2001 | Blackwell | |
| 6,179,772 B1 | 1/2001 | Blackwell | |
| 6,186,941 B1 | 2/2001 | Blackwell | |
| 6,200,259 B1 | 3/2001 | March | |
| 6,213,934 B1 | 4/2001 | Bianco et al. | |
| 6,261,221 B1 | 7/2001 | Tepper et al. | |
| 6,364,824 B1 | 4/2002 | Fitzsimmons | |
| 6,395,799 B1 | 5/2002 | Johnson | |
| 6,418,345 B1 | 7/2002 | Tepper et al. | |
| 6,443,883 B1 | 9/2002 | Ostrow et al. | |
| 6,463,336 B1 | 10/2002 | Mawhinney | |
| 6,560,487 B1 | 5/2003 | McGraw et al. | |
| 6,561,968 B1 | 5/2003 | Dissing et al. | |
| 6,675,048 B2 | 1/2004 | McGraw et al. | |
| 6,792,315 B2 | 9/2004 | Carter et al. | |
| 6,819,210 B2 | 11/2004 | Boynton et al. | |
| 6,839,595 B2 | 1/2005 | Tepper et al. | |
| 6,853,863 B2 | 2/2005 | Carter et al. | |
| 6,853,864 B2 | 2/2005 | Litovitz | |
| 6,856,839 B2 | 2/2005 | Litovitz | |
| 6,955,642 B1 | 10/2005 | Simon | |
| 7,010,353 B2 | 3/2006 | Gan et al. | |
| 7,130,692 B2 | 10/2006 | Brighton et al. | |
| 7,158,835 B2 | 1/2007 | Brighton et al. | |
| 7,175,587 B2 | 2/2007 | Gordon et al. | |
| 2002/0151760 A1* | 10/2002 | Paturu | 600/15 |
| 2002/0165583 A1 | 11/2002 | Tepper et al. | |
| 2003/0095022 A1 | 5/2003 | Boynton et al. | |
| 2003/0158585 A1 | 8/2003 | Burnett | |
| 2004/0210254 A1 | 10/2004 | Burnett | |
| 2005/0124846 A1 | 6/2005 | Pasula | |
| 2005/0182287 A1 | 8/2005 | Becker | |
| 2005/0267355 A1 | 12/2005 | Parker | |
| 2006/0212077 A1 | 9/2006 | Pilla et al. | |
| 2007/0293798 A1* | 12/2007 | Hu et al. | 602/27 |
| 2008/0125618 A1* | 5/2008 | Anderson et al. | 600/14 |

OTHER PUBLICATIONS

An Electrical Device to Make Bones Grow, http://www.thirdage.com/ebsco/files/14707.html, Oct. 21, 2007.

http://www.scielo.br/scielo.php?pid=S0100-879X2006005000030&script=sci_arttext, Nov. 8, 2007.

Pulsed Electromagnetic Fields for Bone Health and Bone Healing, QRS World of Health, http://www.qrsworldofhealth.com/osteoporosis_intro.html, Oct. 9, 2007.

Hiromasa Miura, Application of a Pulsed Electromagnetic Field for the Treatment of Osteoporosis, Department of Orthopaedic Surgery, Kyushu University, Nov. 8, 2007.

Kyle Chang, Walter Hong-Shong Chang, Yen-Hsin Yu, Chung Shih, Pulsed Eectromagnetic Field Stimulation of Bone Marrow Cells Derived from Ovariectomized Rats Affects Osteoclast Formation and Local Factor Production, May 14, 2003, (Abstract Only), http://www3.interscience.wiley.com/search/allsearch?mode=viewselected&product=journal&ID=107061128&view_selected.x=69&view_selected.y=9.

Jitendra Behari and Jayanand, Low Level Pulsed Radio Frequency Field and Its Remedial Effect on Osteoporosis and Bone Fracture, Progress in Electromagnetics Research Symposium 2005, Aug. 22-26, 2005, pp. 736-739 Hangzhou, China.

Lirani-Galvãão, C.T. Bergamaschi, O.L. Silva and M. Lazaretti-Castro, Electrical Field Stimulation Improves Bone Mineral Density in Ovariectomized Rats, Brazilian Journal of Medical and Biological Research, Nov. 2006, 1501-1505; http://www.scielo.br/pdf/bjmbr/v39n11/6295.pdf.

Paul Andrew Glazer, Lian Clamen Glazer "Electricity: The History and Science of Bone Growth Stimulation for Spinal Fusion." Orthopaedic Journal at Harvard Medical School. http://www.orthojournalhms.org/ojhms2002/manuscripts/manuscripts-01.htm. Mar. 12, 2009.

* cited by examiner

Testing Results

| Voltage | 500Hz, 5% Duty Cycle | | 500Hz, 10% Duty Cycle | | 200Hz, 5% Duty Cycle | |
|---|---|---|---|---|---|---|
| | Magnetic Density(μT) | Avg. Current (Amp) | Magnetic Density(μT) | Avg. Current (Amp) | Magnetic Density(μT) | Avg. Current (Amp) |
| 6 | 7.4μT | 0.09A | 15.7 | | 9 | |
| 7 | 9.1μT | | 16.9 | | 10 | |
| 8 | 10.5μT | 0.12 | 18.5 | 0.2 | 10.5 | 0.15 |
| 9 | 11.9μT | | 19.9 | | 11.1 | |
| 10 | 13.2μT | | 21.1 | | 11.7 | |
| 11 | 14.3μT | | 22.2 | | 12.2 | |
| 12 | 15μT | | 23.3 | | 12.7 | |
| 13 | 16μT | | 24.3 | | 13.2 | |
| 14 | 16.8μT | | 25.1 | | 13.7 | |
| 15 | 17.6μT | | 26 | | 14.1 | |
| 16 | 18μT | 0.17 | 26.8 | 0.33 | 14.6 | 0.24 |
| 17 | 19μT | | 27.5 | | 15 | |
| 18 | 19.5μT | | 28.3 | | 15.5 | |
| 19 | 20μT | | 58 | | 15.9 | |
| 20 | 20.3μT | | 62 | | 16.3 | |
| 21 | 21.5μT | | 65.6 | | 16.7 | |
| 22 | 22μT | | 69 | | 17.1 | |
| 24 | 23μT | 0.22 | 76 | .047 | 17.9 | 0.32 |

FIG. 25

Testing Results

| Voltage | 150Hz, 5% Duty Cycle | | | |
|---|---|---|---|---|
| | Magnetic Density (μT) | | | Average Current (Amp) |
| | X Axis | Z Axis | Y Axis | |
| 6V | 8.5 | 0.7 | 7.9 | 0.13 |
| 7V | 10.2 | 0.8 | 9.5 | 0.15 |
| 8V | 11.8 | 0.9 | 10.9 | 0.16 |
| 9V | 13.3 | 1.1 | 12.5 | 0.17 |
| 10V | 15 | 1.2 | 14 | 0.19 |
| 11V | 16.5 | 1.3 | 15.6 | 0.2 |
| 12V | 18.3 | 1.5 | 17 | 0.21 |
| 13V | 20 | 1.6 | 18.7 | 0.22 |
| 14V | 21.5 | 1.8 | 20.2 | 0.24 |
| 15V | 23.3 | 1.9 | 21.5 | 0.25 |
| 16V | 24.8 | 2 | 23.2 | 0.26 |
| 17V | 26.2 | 2.1 | 24.5 | 0.27 |
| 18V | 28.2 | 2.3 | 26.2 | 0.28 |
| 19V | 29.5 | 2.4 | 28 | 0.3 |
| 20V | 31.5 | 2.6 | 29 | 0.32 |
| 21V | 33.2 | 2.7 | 31 | 0.33 |
| 22V | 34.7 | 2.8 | 32.5 | 0.34 |
| 23V | 36.5 | 3 | 34 | 0.35 |
| 24V | 38 | 3.1 | 35.2 | 0.36 |

FIG. 28

Testing Results

| Voltage | 150Hz, 10% Duty Cycle | | | |
|---|---|---|---|---|
| | Magnetic Density (μT) | | | Average Current (Amp) |
| | X Axis | Z Axis | Y Axis | |
| 6V | 18.9 | 1.2 | 17.5 | 0.22 |
| 7V | 22.5 | 1.5 | 20.8 | 0.27 |
| 8V | 25.8 | 1.7 | 23.9 | 0.3 |
| 9V | 29 | 1.9 | 26.9 | 0.33 |
| 10V | 32.5 | 2.2 | 30.4 | 0.36 |
| 11V | 35.8 | 2.4 | 33.3 | 0.39 |
| 12V | 39 | 2.6 | 36.4 | 0.42 |
| 13V | 42.5 | 2.8 | 39.6 | 0.45 |
| 14V | 45.9 | 3.1 | 42.5 | 0.48 |
| 15V | 49.4 | 3.3 | 45.9 | 0.51 |
| 16V | 52.5 | 3.5 | 48.5 | 0.53 |
| 17V | 55.3 | 3.7 | 52.7 | 0.56 |
| 18V | 59 | 4 | 55 | 0.59 |
| 19V | 62.5 | 4.3 | 58 | 0.63 |
| 20V | 65.5 | 4.6 | 59.7 | 0.65 |
| 21V | 69 | 4.8 | 64 | 0.68 |
| 22V | 72.4 | 5.1 | 67.6 | 0.71 |
| 23V | 75.6 | 5.4 | 69 | 0.74 |
| 24V | 78.5 | 5.6 | 73 | 0.77 |

FIG. 29

Testing Results

| Voltage | 500Hz, 5% Duty Cycle ||| Average Current (Amp) |
|---|---|---|---|---|
| | Magnetic Density (μT) ||| |
| | X Axis | Z Axis | Y Axis | |
| 6V | 4.7 | 0.4 | 4.4 | 0.09 |
| 7V | 5.8 | 0.5 | 5.4 | 0.11 |
| 8V | 6.8 | 0.6 | 6.4 | 0.12 |
| 9V | 7.8 | 0.7 | 7.3 | 0.12 |
| 10V | 8.9 | 0.8 | 8.4 | 0.13 |
| 11V | 10 | 0.9 | 9.3 | 0.13 |
| 12V | 11 | 1.1 | 10.4 | 0.14 |
| 13V | 12.3 | 1.2 | 11.4 | 0.15 |
| 14V | 13.4 | 1.3 | 12.4 | 0.16 |
| 15V | 14.5 | 1.4 | 13.5 | 0.17 |
| 16V | 15.6 | 1.5 | 14.6 | 0.17 |
| 17V | 16.8 | 1.6 | 15.7 | 0.18 |
| 18V | 18.1 | 1.8 | 16.8 | 0.18 |
| 19V | 19.2 | 1.9 | 17.9 | 0.19 |
| 20V | 20.4 | 2 | 19 | 0.2 |
| 21V | 21.6 | 2.1 | 20.1 | 0.21 |
| 22V | 22.9 | 2.3 | 21.3 | 0.21 |
| 23V | 24 | 2.4 | 22.4 | 0.22 |
| 24V | 25.3 | 2.5 | 23.5 | 0.23 |

FIG. 30

Testing Results

| Voltage | 500Hz, 10% Duty Cycle | | | |
|---|---|---|---|---|
| | Magnetic Density (μT) | | | Average Current (Amp) |
| | X Axis | Z Axis | Y Axis | |
| 6V | 11.3 | 1.1 | 10.5 | 0.15 |
| 7V | 13.3 | 1.3 | 12.4 | 0.17 |
| 8V | 15.4 | 1.5 | 14.4 | 0.19 |
| 9V | 17.6 | 1.7 | 16.4 | 0.22 |
| 10V | 19.8 | 1.9 | 18.4 | 0.23 |
| 11V | 22.1 | 2.2 | 20.4 | 0.25 |
| 12V | 24.3 | 2.4 | 22.6 | 0.27 |
| 13V | 26.6 | 2.7 | 24.6 | 0.28 |
| 14V | 28.7 | 2.9 | 26.8 | 0.3 |
| 15V | 30.8 | 3.1 | 28.7 | 0.32 |
| 16V | 33.2 | 3.3 | 31.3 | 0.34 |
| 17V | 35.5 | 3.6 | 33.2 | 0.35 |
| 18V | 37.9 | 3.8 | 35.2 | 0.37 |
| 19V | 40 | 4 | 37.5 | 0.38 |
| 20V | 42.4 | 4.3 | 39.5 | 0.4 |
| 21V | 44.5 | 4.5 | 41.6 | 0.43 |
| 22V | 46.8 | 4.7 | 43.6 | 0.44 |
| 23V | 49.3 | 5 | 46 | 0.46 |
| 24V | 51.7 | 5.2 | 48.4 | 0.48 |

FIG. 31

Testing Results

| Voltage | 200Hz, 5% Duty Cycle | | | |
|---|---|---|---|---|
| | Magnetic Density (µT) | | | Average Current (Amp) |
| | X Axis | Z Axis | Y Axis | |
| 6V | 7.4 | 0.6 | 6.9 | 0.11 |
| 7V | 8.9 | 0.7 | 8.4 | 0.14 |
| 8V | 10.4 | 0.8 | 9.8 | 0.15 |
| 9V | 11.9 | 1 | 11.1 | 0.16 |
| 10V | 13.4 | 1.1 | 12.5 | 0.17 |
| 11V | 14.8 | 1.2 | 13.8 | 0.18 |
| 12V | 16.3 | 1.4 | 15.2 | 0.19 |
| 13V | 17.8 | 1.5 | 16.7 | 0.2 |
| 14V | 19.4 | 1.6 | 18 | 0.21 |
| 15V | 20.8 | 1.8 | 19.5 | 0.22 |
| 16V | 22.4 | 1.9 | 20.8 | 0.23 |
| 17V | 23.8 | 2 | 22.2 | 0.25 |
| 18V | 25.4 | 2.1 | 23.7 | 0.26 |
| 19V | 26.8 | 2.2 | 25 | 0.26 |
| 20V | 28.2 | 2.4 | 26.5 | 0.27 |
| 21V | 30 | 2.5 | 28 | 0.28 |
| 22V | 31.5 | 2.7 | 29.4 | 0.3 |
| 23V | 33.1 | 2.8 | 31 | 0.31 |
| 24V | 34.5 | 2.9 | 32.2 | 0.32 |

FIG. 32

PIEZOELECTRIC, MICRO-EXERCISE APPARATUS AND METHOD

BACKGROUND

1. The Field of the Invention

This invention relates generally to reduction in bone mass associated with inactivity, such as occurs whenever a limb is immobilized by a cast for an extended period of time, and more particularly to apparatus and methods to promote exercise on a cellular level when actual exercise motion by the limb is not available.

2. The Background Art

Bones represent a curious structure, often referred to in the prior art as "not well understood." In space, such as during missions to the moon, extended orbits, work within the space station, during healing of a broken bone immobilized in a cast for typically six weeks or more, and the like, science has studied the loss of bone mass. The lack of exercise appears to relate to the loss of bone mass.

Moreover, bone mass may be lost at a greater rate in the absence of exercise then it can typically be regained upon resumption of exercise. Thus, what is needed is an apparatus and method to apply exercise to a bone structure that is immobilized as a result of casting, traction, immobilization, or the like.

BRIEF SUMMARY OF THE INVENTION

An apparatus and method in accordance with the invention may include a frame forming a basic structure of a device such as a removable cast or splint. The frame may or may not include a wrap. Typically, a wrap may be provided for warmth, comfort through isolation of the frame from the injured member, or the like. The frame, the wrap, or both may include embedded electromagnetic coils. The electromagnetic coils may be programmatically controlled to energize with a timing and sequence selected to render treatment effective and to minimize cancellation of electromagnetic fields created by the coils.

The embedded coils may operate to set up dynamic electromagnetic fields. Dynamic electromagnetic fields create electrical currents as a result of passing through conductors or around conductors. Various equations of physics define the electromagnetic activities of a magnetic flux as it rises and falls in density with respect to time. For example, motors of the electrical type operate on the responses of moving parts to the changing of electromagnetic fields within them. Meanwhile, those electromagnetic fields are set up by electrical currents operating in coils within those motors.

By the same token, moving an electromagnetic fields with respect to conductors or moving conductors through electromagnetic fields induces currents in conductors.

Accordingly, in certain embodiments of apparatus and methods in accordance with the invention, electromagnetic fields as they rise and fall in intensity in a localized area may induce currents within bone materials. Bone material is piezoelectric. Capitalizing on the piezoelectric nature of the structural material of bone, an apparatus and method in accordance with the invention may induce voltages across portions of bone material as a result of the rising and falling of electromagnetic force applied dynamically. That is, as the flux density of the electromagnetic coils rises and falls, it creates electrical currents and voltages in conductive materials nearby.

In certain embodiments of an apparatus and method in accordance with the invention, the induced voltages and currents operate on the piezoelectric cellular structures of bone matter to stress the bone. Literally, the bone material distorts with the presence of the applied voltage. Thus, at a very low level, bone material may be stressed and strained, that is, loaded with force or pressure and stretched or compressed accordingly, with the application of electrical voltage.

When bones are exercised, just as muscles are exercised, the forces or loads applied thereto stretch or compress the affected tissue. The contraction of muscles is well appreciated. Likewise, muscles may extend or contract as they operate to move bone structures within the body. It is not as well understood that any time the supposedly "fixed" length of a bone is put under load, that bone stretches, compresses, bends, or a combination thereof in some slight amount compared to the much greater amount of such deflection or distortion by a muscle.

The need to exercise muscles is well understood. However, the need to exercise bones is less well understood, and perhaps not understood by many who readily accept the need for muscle exercise. Thus, one may think of conventional exercise as including a process of stressing the bones in a way that causes them to stretch, compress, bend, or a combination thereof. Bones appear to respond to exercise by building mass. When bones are immobilized, an apparatus and method in accordance with the invention may still create at a cellular or microscopic level the conditions that exercise would have created. A lack of exercise corresponds to a lack of piezoelectric activity in the bone.

As bones distort, they behave piezoelectrically. Just as an electrical voltage applied to a piece of bone causes a distortion in that piece of bone, imperceptible to the eye, but perceptible by various measurement techniques, the reverse process also works. For example, if a voltage applied to a piezoelectric material distorts the piezoelectric material, then distortion of the piezoelectric material will create a voltage across it.

For example, if walking about on the earth creates healthy bones, and if exercise tends to build bone mass, while a lack of exercise tends to lose bone mass, an individual cell may be seen as a tiny embedded element within that bone structure. As far as that cell is concerned, it does not know about the foot running on the ground, or the arm lifting weights. Rather, that small cell of bone only responds to the stress and strain it undergoes.

In response to that stress and strain, and the piezoelectric signals of electricity generated as a result of the stress and strain on that cell of bone, the bone responds. The bone responds to exercise by developing bone mass. Therefore, the bone mass decreases when a bone is cast for healing, such as a broken arm or broken leg. Likewise, in space, where bones are not required to maintain the support structure of the body mass of an individual against gravity, they do not see the common, daily, continual stress and strain of simply living.

Thus, loss of bone mass may be attributed in large part to a lack of exercise. This appears to also be corroborated by the correlations between osteoporosis and exercise. As people become immobile, they tend to increase the porosity of bone and decrease its mass.

Accordingly, an apparatus in accordance with the invention provides piezoelectric, micro-exercise for bone structures replicating the conditions that would typically exist if that bone mass were able to be exercised conventionally.

In certain apparatus, the frame and the covering pad may both include magnetic coils. Energizing the coils in the frame, in the pad, or both may occur alone, separately, or in a coordinated fashion.

Meanwhile, a controller may control the energizing of electromagnetic coils in the pad, in the frame, or both. The controller may be programmed by a physician to input a particular piezoelectric exercise regimen proposed. In certain embodiments, an individual may be able to program a controller controlling the energizing of coils in the padding or frame according to how the user is feeling.

Coils may be installed in various locations and selectively activated according to a desired effect. For example, in certain embodiments, the coils may be placed in the bed of a sole of a boot cast. Likewise, coils may be placed along the vertical uprights in the cast. Coils may be placed in other strategic locations according to the desired process and effect implemented.

In certain embodiments, coils may be sequenced in a series of overlapping rising and magnetic fields in a particular area. In other embodiments, coils may be sequenced in a manner that provides that the magnetic field from one coil may be completely collapsed before the magnetic field on the other arises. Thus, interaction between coils may be minimized.

For example, in a transformer, a "bucking" arrangement may be set up in which two transformers are basically transforming against one another. The result is a generation of heat, expenditure of energy, but no net energy is really transferred across systems. Thus, in certain embodiments, the programmatic controls of the controller may assure that within a reasonable proximity of one another, various coils are not energized and de-energized at a rate and proximity that will negate the influence of one coil by another. This makes energy conservation sense as well as therapeutic sense in that the magnetic field is permitted to penetrate as far as possible and act alone or in concert, rather than against other magnetic fields set up by other coils.

In other methods and apparatus in accordance with the invention, coils may be designed to have various diameters, numbers of turns, air cores, or electromagnetic cores according to the desire for direction and intensity of magnetic field. For example, that flux density in a magnetic core may provide much better alignment and penetration.

It has also been suggested that bone response to electromagnetic stimulation is ineffectual after about thirty minutes of treatment. This is consistent with other experiments and experiences with nutrition. The body must deliver energy, and depends on the catalytic minerals in the cells to provide the energy release required to support cell activity.

Meanwhile, the body relies on various chemical transport processes to carry away waste by-products, the chemical reactants resulting from energy generation by cells. Those reactants are often rich in reactive materials or "free radicals." Anti-oxidants neutralize free radicals and prevent them from causing other chemical damage to cells as they are transported through the cells and away to the body's waste handling systems. Thus, minerals catalyze the chemical breakdown of energy materials, while anti-oxidants neutralize the by-products of energy released in the cells.

Similarly, whenever any process overruns or outruns other bodily processes, the overall system cannot operate any faster than its slowest intermediate process. In any chemical reaction, it is typical that several chemical reactions are actually taking place. The overall system of chemical reactions can proceed no faster than the rate-limiting reaction that every other reaction is waiting on.

Thus, in apparatus and method in accordance with the invention, rather than apply therapy in every case a single time everyday, shorter periods of therapy may be applied at intervals extended throughout the day. Thus, the other bodily processes can keep up with the bone stimulation in order to provide a balanced building process.

In certain embodiments, a duty cycle for an apparatus in accordance with the invention may involve the system being on for one minute and off for 59. In other embodiments, the apparatus may be on for 10 minutes and off for 50 minutes every hour. Meanwhile, the individual coils in the apparatus may be on for only a very small fraction of the duty cycle, inasmuch as the coils are activated in sequence.

In certain embodiments, the prescribed system of electromagnetic activity from the coils of the frame, covering, or both, may be tracked and correlated with x-rays in order to show the response of a particular area of bone mass to an apparatus and method in accordance with the invention. Thus, the use of periodic x-rays in assessing the bone density of an immobilized limb may be used to alter the regimen prescribed, and may be used to complete the regimen in body one location, while continuing it in another in order to provide a uniform development of bone mass.

In certain embodiments, an integrated dressing may be used having electromagnetic coils operated by the system in accordance with the invention. Thus, a dressing, a frame, a covering or wrap for the member may each be used individually, or any combination thereof may be used in order to provide electromagnetic flux densities required and the dynamic rising and falling thereof in order to provide the bone density management or intervention required.

In certain embodiments of an apparatus in accordance with the invention, a wear layer or witness layer may be provided on the foot bed or sole of a boot cast. For example, removable boot casts provide a foot bed similar to a shoe. A wear layer may be provided such as a two-layer lamination having a comparatively easily worn off top layer of one color with a more robust substrate therebelow. Thus, if an individual walks prematurely on the boot cast, then the witness layer may show the contrasting color of the substrate through a ruptured or worn off outer portion, thus providing an absolute verification that the foot has been pressuring, wearing, or otherwise active on the foot bed.

In certain embodiments, comparatively flat coils may be embedded in wraps (coverings), structures of a frame, such as the foot bed, vertical uprights, collars, straps, and the like in order to provide penetration normal (perpendicular) to the surfaces about which those portions of the apparatus lie. Thus, electromagnetic flux may be directed into the bodily member for which bone density intervention is desired. In other embodiments, the coils may be aligned in order to provide a flux that flows parallel to the surface, and thus at a greater distance eventually curves in to and travels axially along the subject member being treated. Nevertheless, a particularly effective and lightweight system may be made very flexible by a large distribution of small coils embedded within a covering, frame member or the like.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 25 is a table of testing results illustrating an array of voltages at various frequencies and duty cycles with the effective magnetic density in micro Teslas and the corresponding currents running in the various coils;

FIG. 28 is a chart illustrating a series of experiments indicating a series of voltages with the frequency and duty cycle corresponding thereto in the x, y, and z axis for a particular embodiment of an apparatus in accordance with the invention;

FIG. 29 is a table of magnetic flux densities for a particular set of voltages and resulting current amperages for a 150 Hertz cycling of an apparatus in accordance with the invention operating on a 10 percent duty cycle;

FIG. 30 is a table of magnetic flux densities for a particular set of voltages and resulting current amperages for a 500 Hertz cycling of an apparatus in accordance with the invention operating on a 5 percent duty cycle;

FIG. 31 is a table of magnetic flux densities for a particular set of voltages and resulting current amperages for a 500 Hertz cycling of an apparatus in accordance with the invention operating on a 10 percent duty cycle;

FIG. 32 is a table of magnetic flux densities for a particular set of voltages and resulting current amperages for a 200 hertz cycling of an apparatus in accordance with the invention operating on a 5 percent duty cycle;

DETAILED DESCRIPTION OF THE PREFERRED EMBODIMENTS

Figure 1:
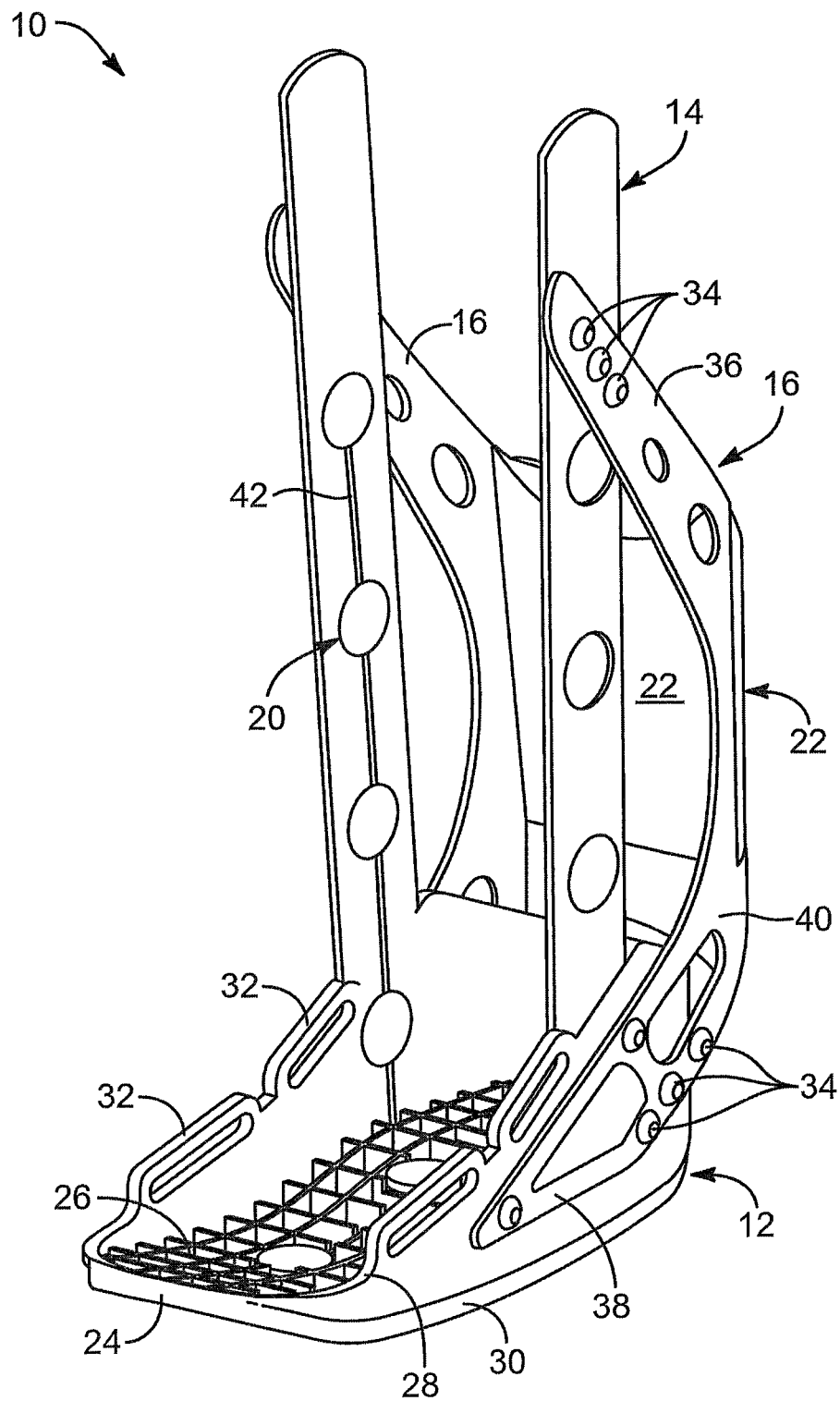
FIG. 1 is a perspective view of one embodiment of a boot cast having a system of vertical uprights with an attached bracket secured to the uprights and the foot bed of the boot cast in order to support a controller and power pack.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, an apparatus 10, such as a boot cast or the frame of a boot cast, may include a base 12. In certain embodiments, the base 12 may be made of plastic or another suitable polymer or reinforced polymer. For example, when the apparatus 10 is a boot cast, the base 12 or portion thereof may serve as the foot bed on which the foot of a user will ultimately rest. Likewise, the base 12 also may serve as the fundamental structure that contacts the ground when the boot cast apparatus 10 is used in a walking configuration.

In certain circumstances, an individual may be provided with a cast, splint, or other similar apparatus 10 for immobilizing a bodily member. At some point, the apparatus 10 may be converted and used to actually support limited mobility (e.g., be walked upon) as the injured member has achieved a degree of healing that will permit some partial use.

In certain embodiments, struts 14 or uprights 14 may extend from the base 12. Typically, the struts 14 may be fixed with respect to the base 12 in order to rigidize the injured member. In certain embodiments, the struts 14 may be flexibly connected to the base 12.

In certain embodiments, a rack 16 may secure to the struts 14. Typically, the rack 16 may serve multiple functions. For example, the rack 16 may serve to support auxiliary equipment for operating the apparatus 10 in accordance with the invention. Batteries, controllers 22 and the like may be mounted to the rack 16 away from the struts in the base 12 that are therapeutically operative for rigidizing the bodily member.

By the same token, the rack 16 may also serve to provide additional strength, rigidity, or stiffness to the struts 14. Thus, with the addition of the rack 16, the struts 14 may be downgraded in their structural stiffness or strength. However, in alternative embodiments, the struts 14 may be constructed to perform their function entirely alone, and the rack 16 may be added for a secondary function such as carrying auxiliary equipment.

Certain embodiments may include a pad 18 (not shown in FIG. 1; refer to FIGS. 33-48 generally, et. seq.) or wrap 18. The pad 18, or wrap 18 as it may also be referred to, provides multiple functions. At a basic physical level, the pad 18 provides stress distribution against prominent parts of the bodily member and pressure relief against the loading of skin and muscle by the presence of the base 12 or struts 14, and the like.

At another level, the pad 18 may operate as a holder, distributor, and locator for multiple electromagnetic coils in the apparatus 10 in order to apply electromagnetic flux to various portions of the bodily member. Thus, instead of, or in addition to, the electromagnetic coils located in the struts 14 and rack 16, the pad 18 may include electromagnetic coils developed for electromagnetic portions of therapies applied to the bones of the immobilized member placed inside the apparatus 10.

Referring specifically to FIGS. 1-9, and more generally to FIGS. 1-22, the apparatus 10 may include various sources 20. Typically, the sources 20 are electromagnetic force coils or coils of conductors providing electromagnetic fields as a result of electric current passing through the conductors of the coils. The sources 20 of electromagnetic flux may be distributed about the base 12 and struts 14 of the frame of the apparatus 10. Likewise, the sources 20 may be distributed throughout the pad 18.

In certain embodiments contemplated, a controller 22 operates to control one or more of the current, the wave form of the current, the voltage, the time of operation, any combination thereof, and so forth for the sources 20 distributed in the pad 18, the rack 16 or frame 16 made up with the base 12 and strut 14 as the structural elements of the apparatus 10.

In general, the base 12 may include a bed 24 or foot bed 24 on which the foot of a user is supported. The bed 24 may be formed of a solid, of a porous solid, of a ribbed solid, including ribs 26 stiffening the base 12 and bed 24 while minimizing weight, or the like. Thus, an expanded polymer, a ribbed polymeric molding, or the like may form a bed 24 having ribs 26 to add stiffness while minimizing weight a user must lift.

In the illustrated embodiment, a wall 28 may substantially surround the bed 24, protecting against incursion by dirt, water, debris, and the like.

Meanwhile, the wall 28 forms an outermost edge, rib, or stiffener, ultimately providing additional section modulus for the bed 24 and base 12. For example, the wall 28 may extend substantially higher than the ribs 26, inasmuch as the foot of a user, in the illustrated embodiment, may fit down between the walls 28, on either side of the base 12.

Padding, a witness layer, or other treatments may be placed on top of the ribs 26 of the foot bed 24 or bed 24. A witness layer or surface may be configured to detect pressure, wear, or other time-inappropriate use by a user. For example, a thin layer of material that is easily damaged may be placed on top of a more robust layer such as a foam pad or solid layer of material on the ribs 26. Thus, any pressure, or any significant wear may be detected by damage to the thin uppermost, fragile, witness layer, signifying that a user has walked on the apparatus 10 or otherwise applied weight to the base 12 and bed 24 that is inappropriate at the particular time according to the prescription of medical personnel. A witness layer may be on the bottom of the sole 30 instead of or in addition to a witness layer on the foot bed 24.

A base 12 may be provided with a sole 30 for actually accepting the pressure and wear of use on a walking surface. For example, in a regimen assigned to a person having a broken leg, an individual may be prohibited from weighting the bed 24 and base 12 of the apparatus 10 for a period of weeks. Thereafter, however, the individual may be prescribed certain weighting of the apparatus 10, such as by a light weight placed thereon while the user walks on crutches. Ultimately, the individual may be instructed to place full weight on the foot, and consequently on the ribs 26 and base 12, in order to resume walking and other conventional exercise. As an individual begins to walk on the base 12, a sole comparatively softer and more flexible 30 may protect against undue wear on the more rigid parts of the base 12, while also providing a certain amount of cushioning against the hard and abrasive materials of a sidewalk or street.

Referring to FIGS. 1-9, while continuing to refer generally to FIGS. 1-22, the base 12 may be provided with loops 32 or other securement devices 32 such as rivets, screws, apertures, glue, hook-end-loop fasteners, or the like in order to secure straps thereto. Loops 32 may extend vertically up or horizontally out from the top edges of the wall 28. Loops 32 may be hinged or rigid.

Typically, straps passing through the loops 32 on either side or either wall 28 on the left and right sides of the apparatus 10 may secure the apparatus 10 to an appendage of a user. Likewise, inasmuch as the apparatus 10 is typically a removable device 10 in the illustrated embodiment, straps through the loops 32 may provide securement of the apparatus 10 to an appendage at a comfortable level of snugness (e.g., tension, and thus pressure).

For example, a pad 18 may surround a foot on the bed 24 and underneath straps passing through the loops 32. Accordingly, a user may secure the straps through the loops 32 at a tension calculated to provide a degree of securement, balanced with a degree of comfort in view of the pad 18 about the foot of a user.

A series of fasteners 34 may secure a rack 16 to the base 12 and struts 14. Typical fasteners may include screws, bolts, glue, ultrasonic welding, or the like. Typically, fasteners 34 may be arranged in sufficient number to provide a substantially rigid connection between the rack 16 and the struts 14 and base 12. Fasteners 34 may be configured as a design element.

In alternative embodiments, some degree of flexibility may be desired. Accordingly, movable or pivotable fasteners 34 may be used as pivot points. In alternative embodiments, flexible fasteners 34 providing pivoting may be implemented. However, in one common embodiment, the fasteners 34 may triangulate and thereby rigidize the rack 16 with respect to the base 12, the strut 14, and both. Likewise, fasteners 34 may fix the struts 14 with respect to the base 12.

In certain embodiments, the rack 16 may be configured as a bracket 16 for mounting the controller 22. For example, a top portion 36 of the bracket 16 may be mounted by fasteners 34 to the struts 14. Meanwhile, a lower portion 38 or bottom portion 38 of the bracket 16 or rack 16 may secure to the base 12. Meanwhile, a central portion 40 or center portion 40 of the rack 16 or bracket 16 may secure the controller thereto. Thus, the upper and lower portions 36, 38 may stand off or place away from the struts 14 the central portion 40 securing the controller 22. Thus, the controller 22 riding on the central portion 38 may be spaced away a suitable distance to permit comfortable retention of the bodily member placed in the apparatus 10.

Wires 42 may connect between the controller 22 and the various sources 20 of electromagnetic force. Accordingly, wires 42 may be embedded within the base 12, struts 14, and elsewhere by way of appropriate paths. The wires 42 may represent a single circuit or many circuits providing for individual sequencing and control of the various sources 20 distributed about the apparatus 10 in the struts 14, base 12, pad 18, and the like.

Figure 2:
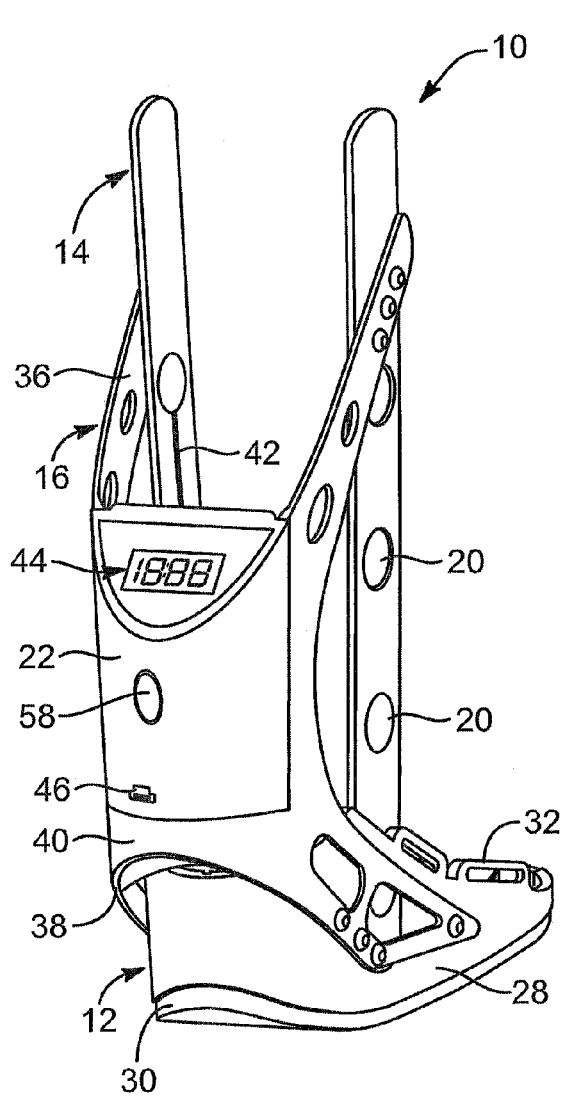
FIG. 2 is a rear quarter perspective view of an apparatus in accordance to the embodiment of FIG. 1.
Figure 3:
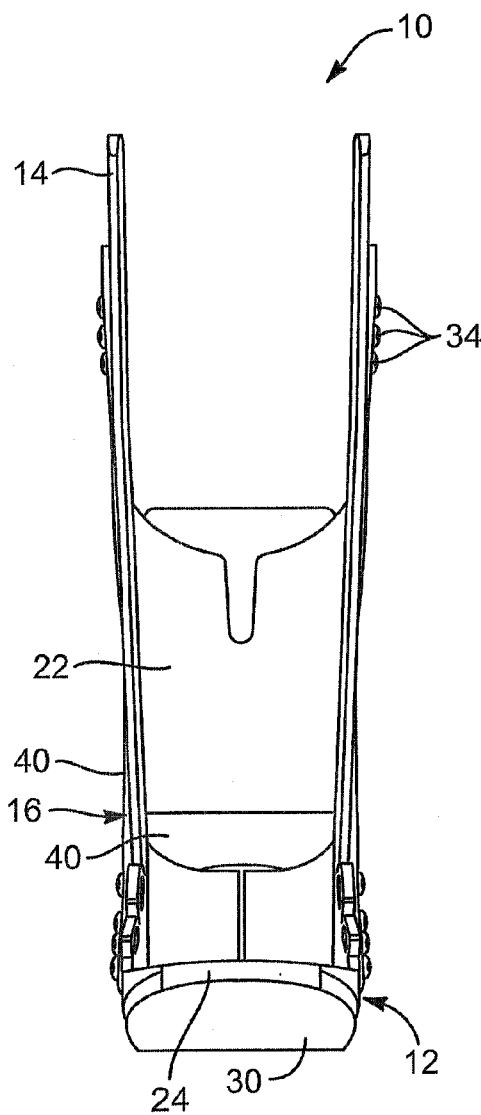
FIG. 3 is a front elevation view of the apparatus of FIGS. 1-2.
Figure 4:
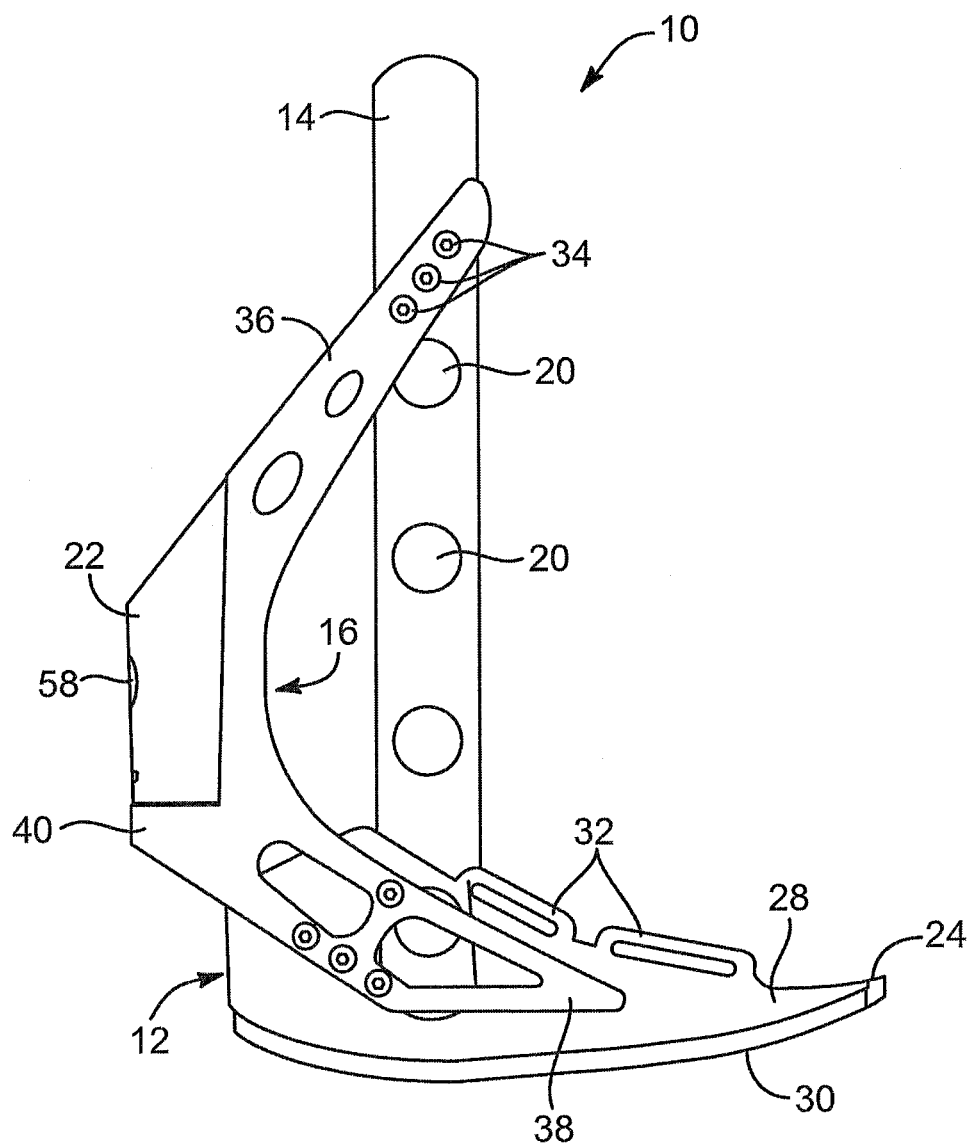
FIG. 4 is a right side elevation view of the apparatus of FIG. 1.
Figure 5:
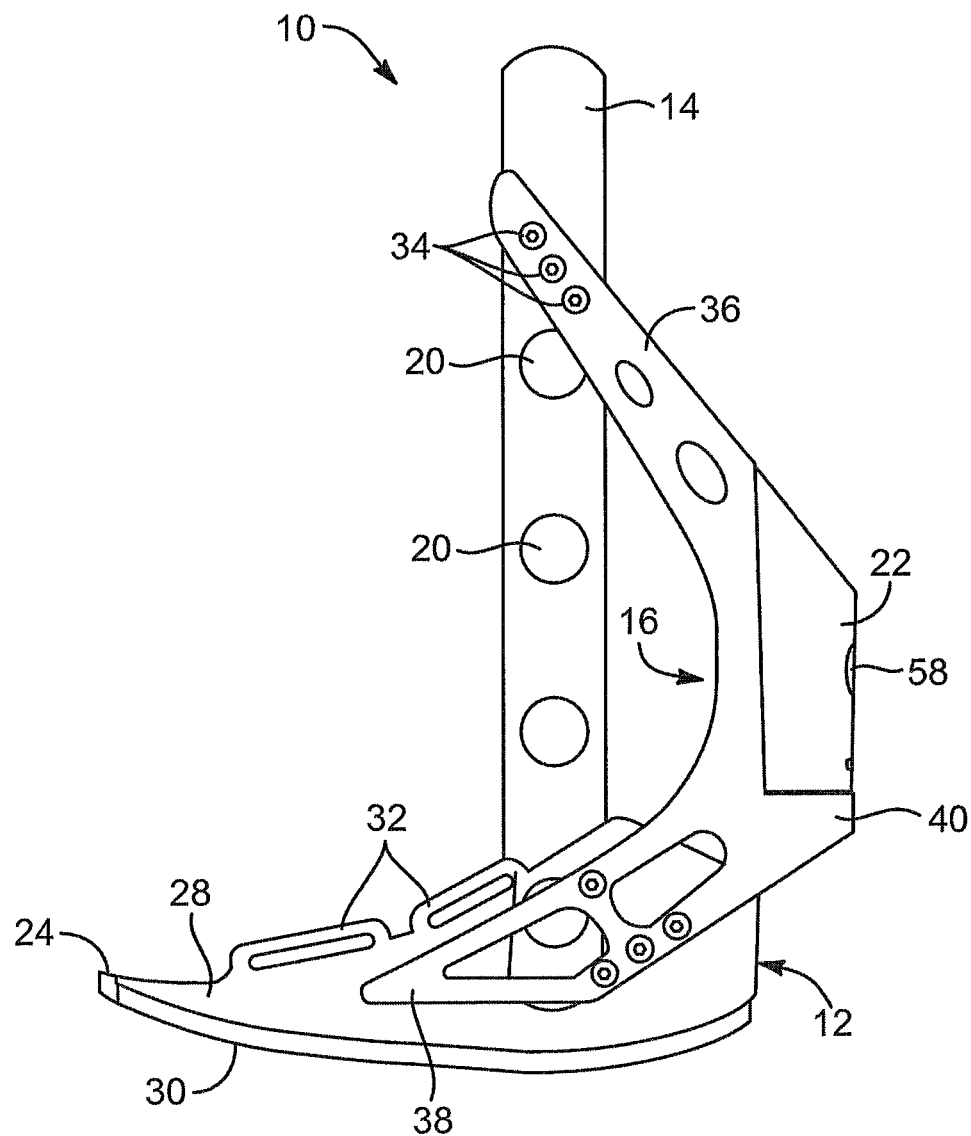
FIG. 5 is a left side elevation view of the apparatus of FIG. 1.
Figure 6:
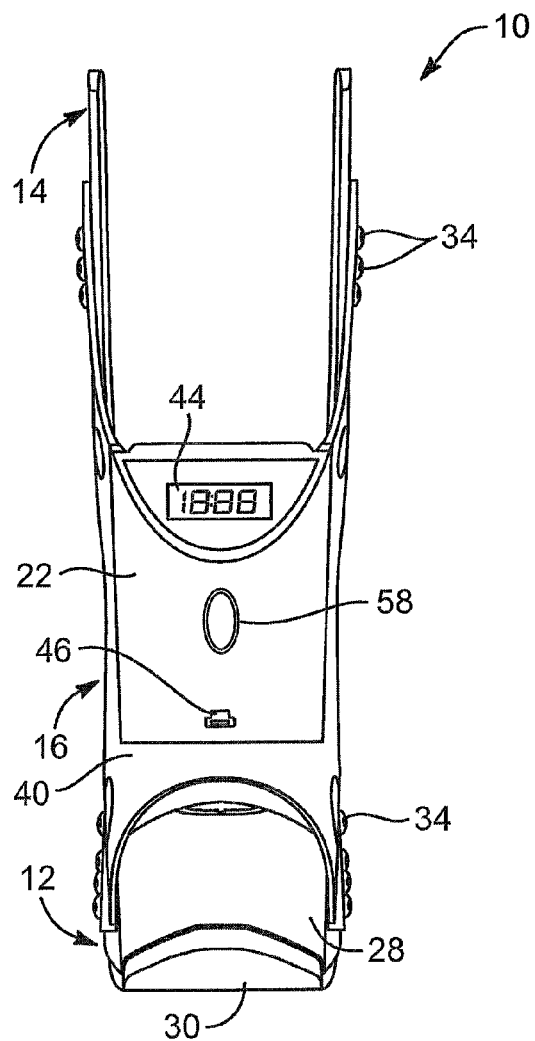
FIG. 6 is a rear elevation view of the apparatus of FIG. 1.
Figure 7:
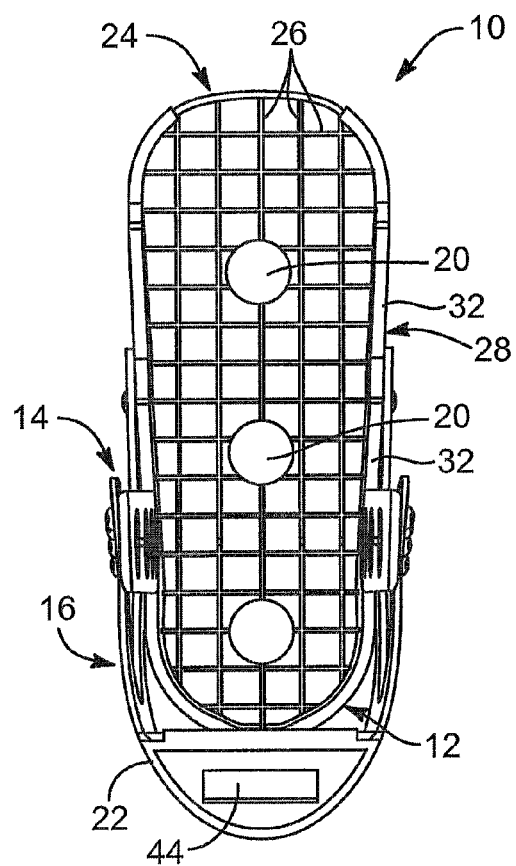
FIG. 7 is a top plan view of the apparatus of FIG. 1.
Figure 8:
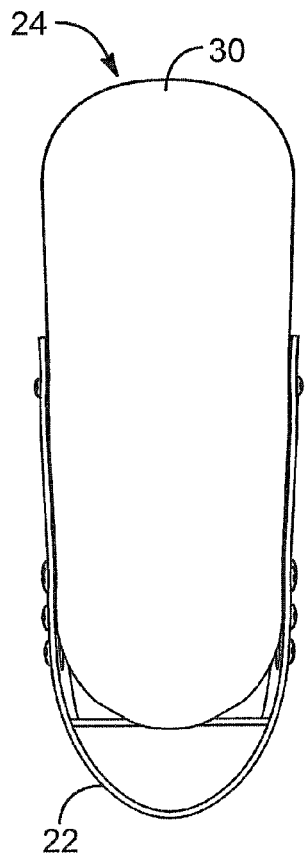
FIG. 8 is a bottom plan view of the apparatus of FIG. 1.
Figure 9:
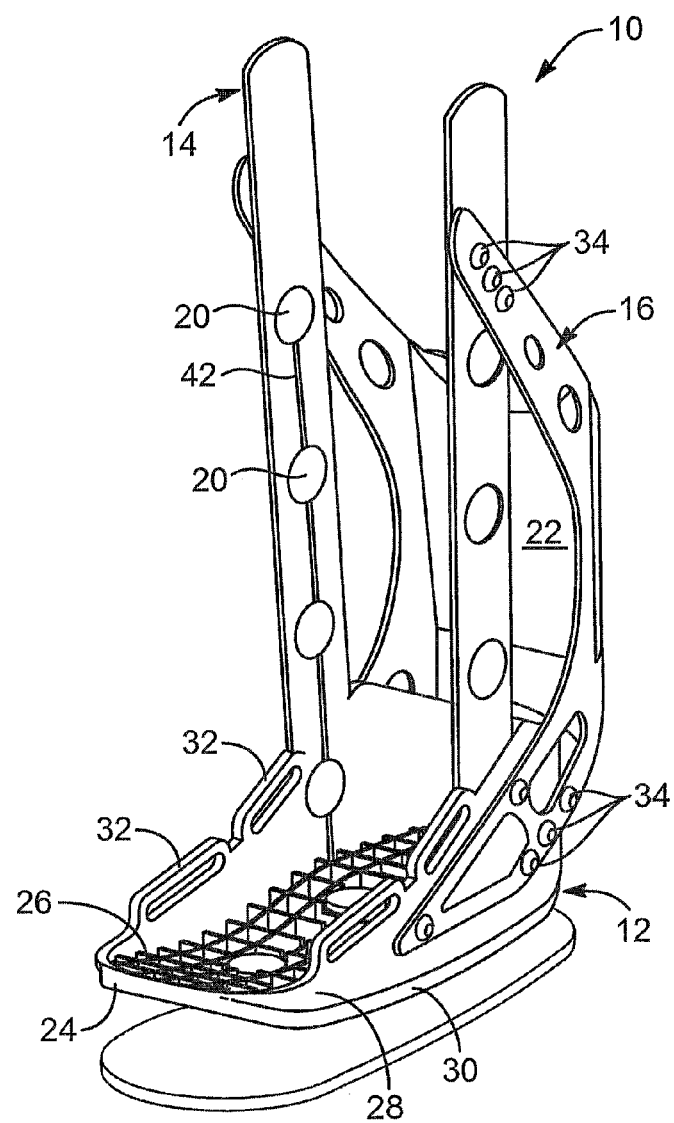
FIG. 9 is a front quarter perspective view of the apparatus of FIG. 1.
Figure 10:
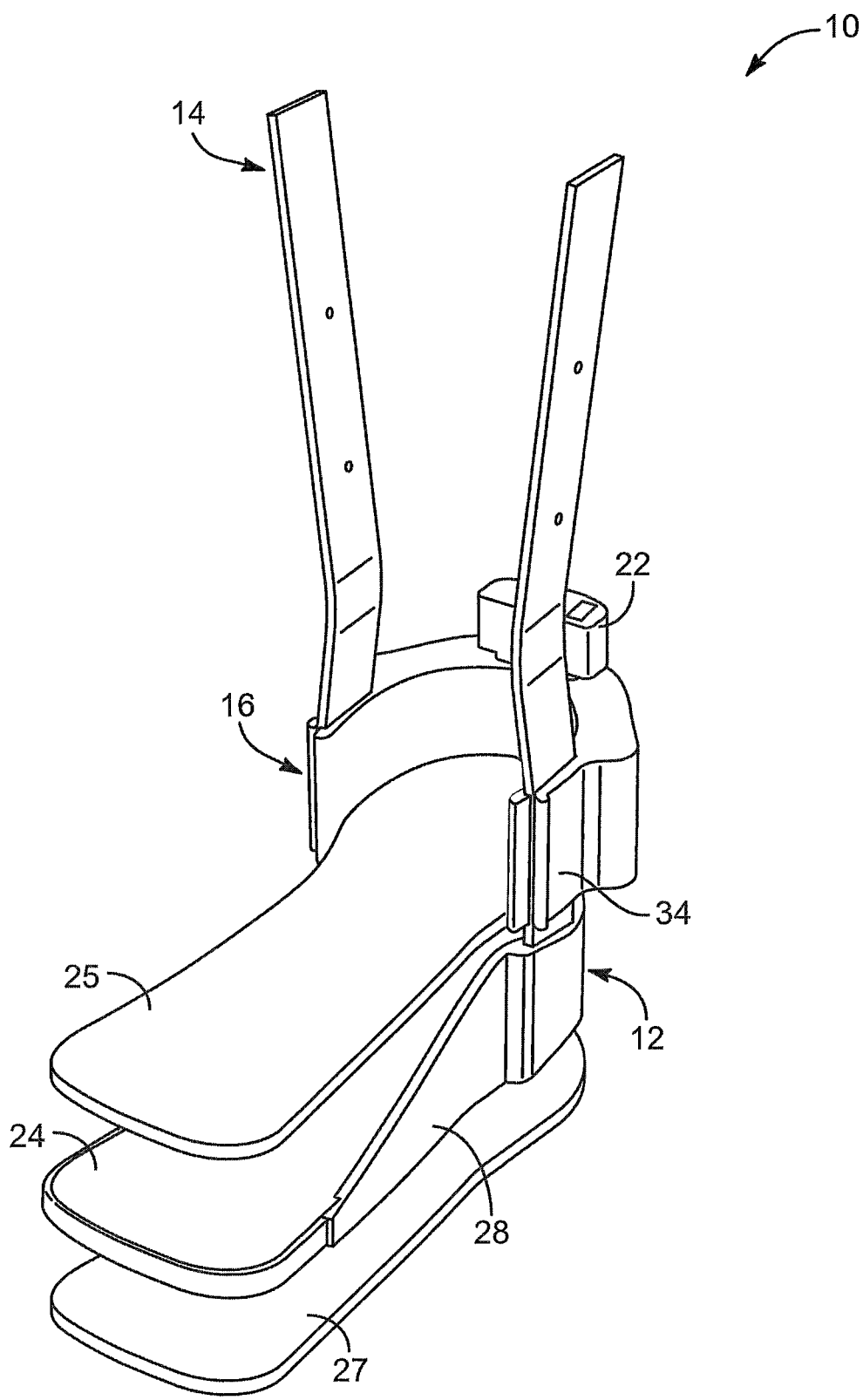
FIG. 10 is a front quarter perspective view of an alternative embodiment of an apparatus in accordance with the invention.
Figure 11:
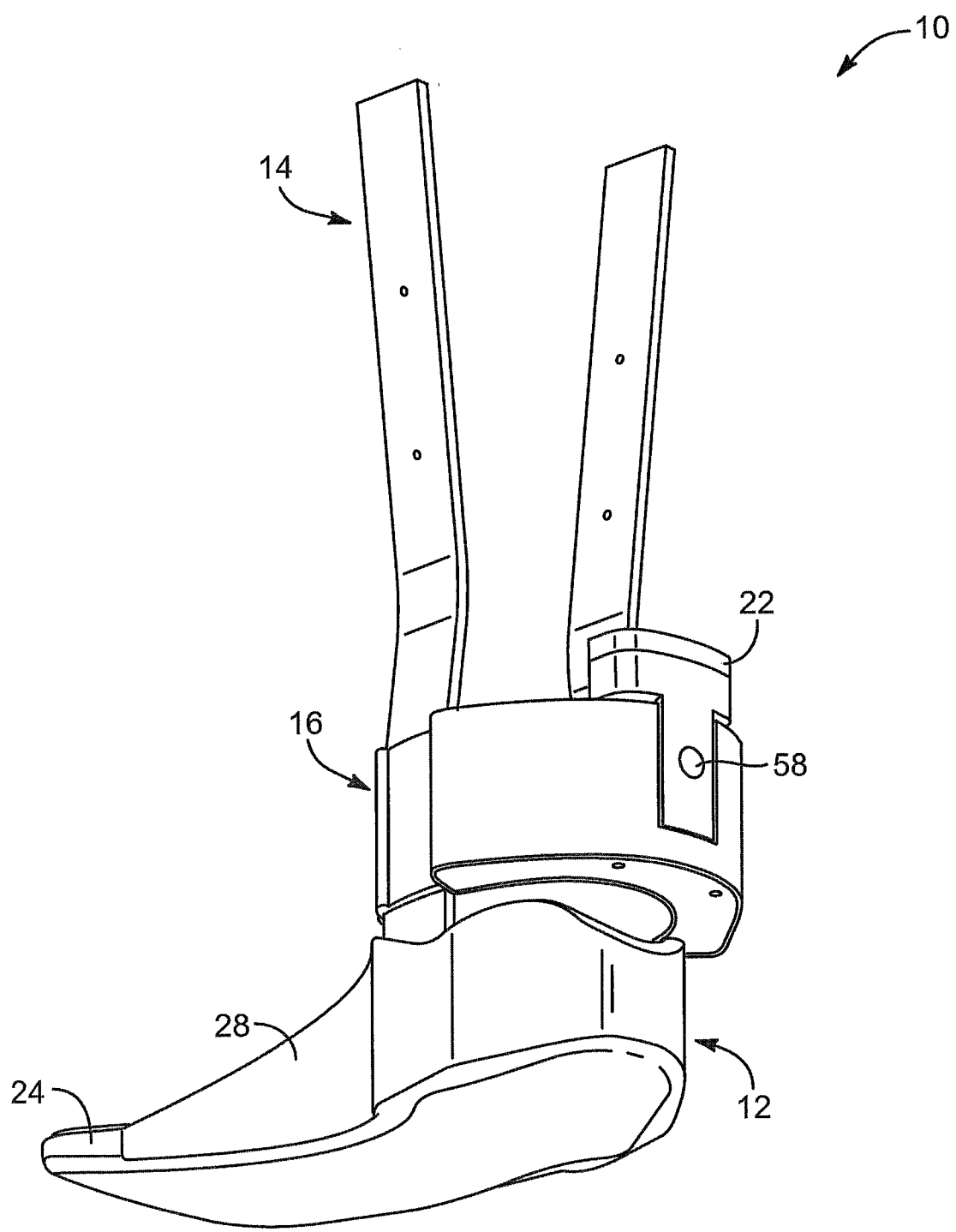
FIG. 11 is a bottom quarter perspective view from a rear quarter of the apparatus of FIG. 10.
Figures 12, 13:
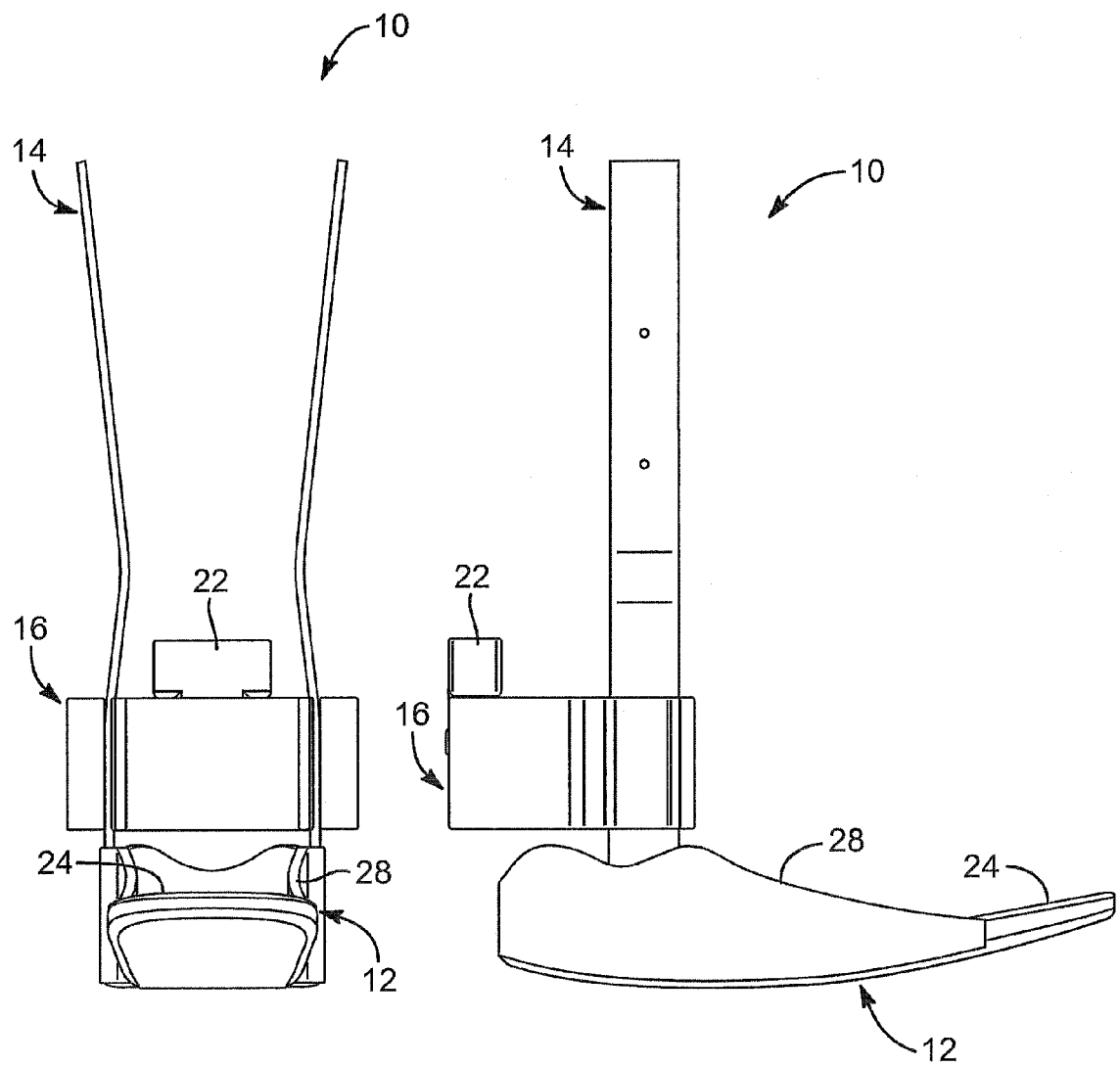
FIG. 12 is a front elevation view of the apparatus of FIG. 10.
FIG. 13 is a right side elevation view of the apparatus of FIG. 10.
Figures 14, 15:
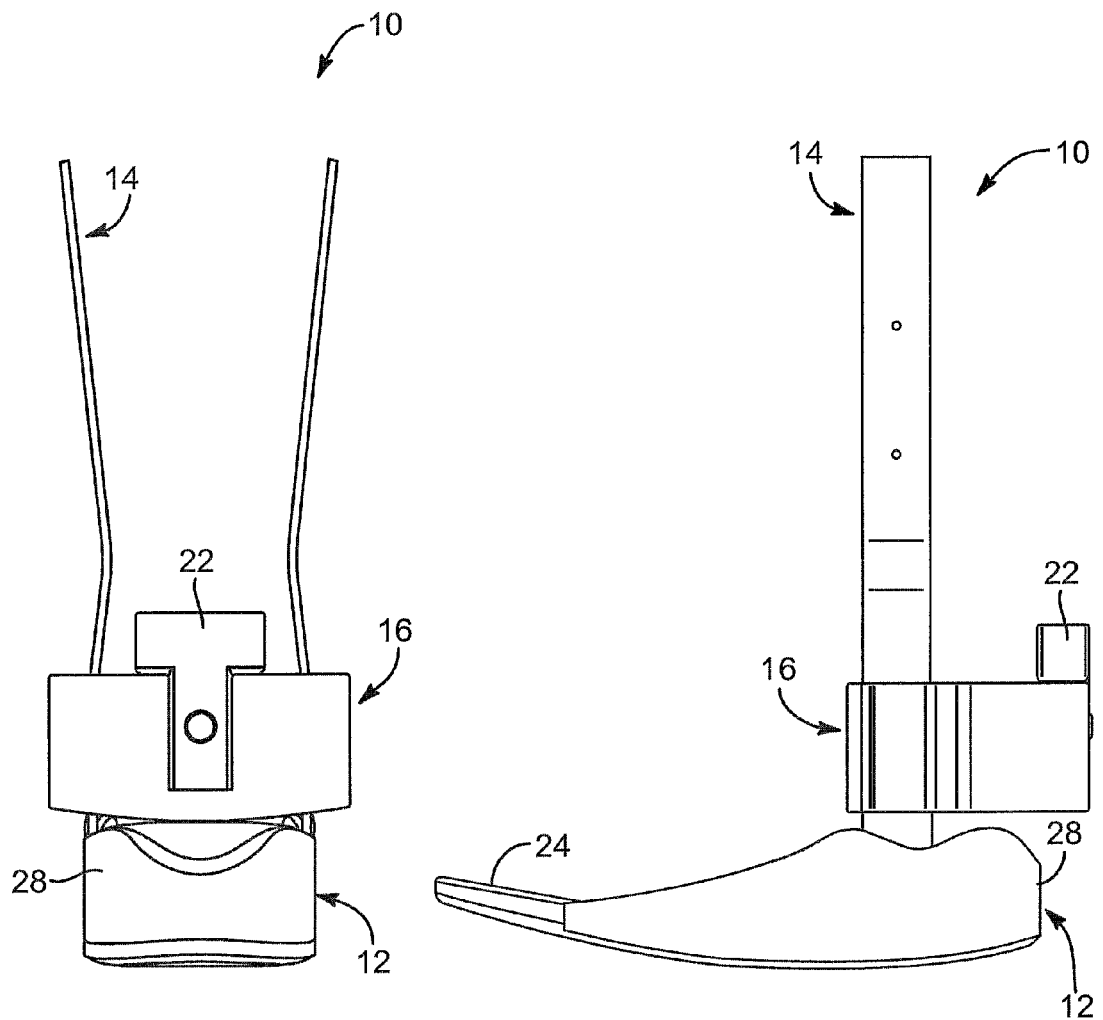
FIG. 14 is a rear elevation view of the apparatus of FIG. 10.
FIG. 15 is a left side elevation view of the apparatus of FIG. 10.
Figure 16:
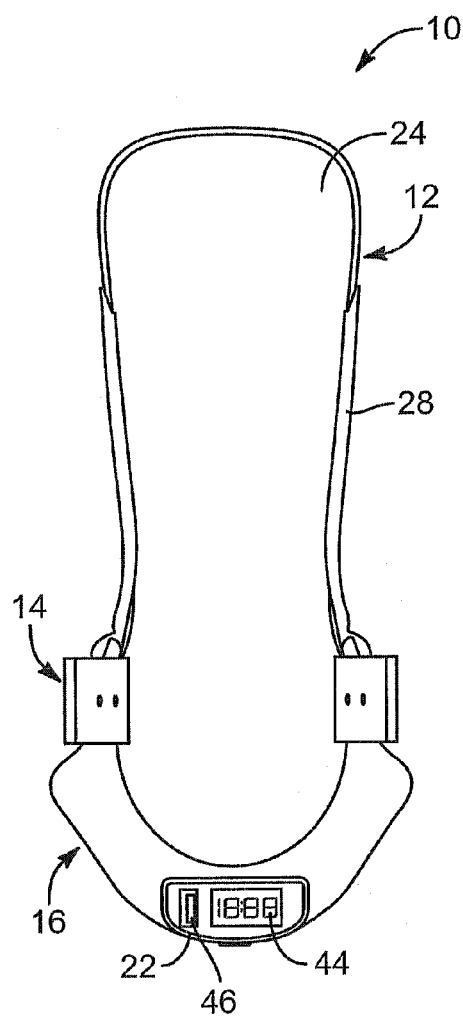
FIG. 16 is a top plan view of the apparatus of FIG. 10.
Figure 17:
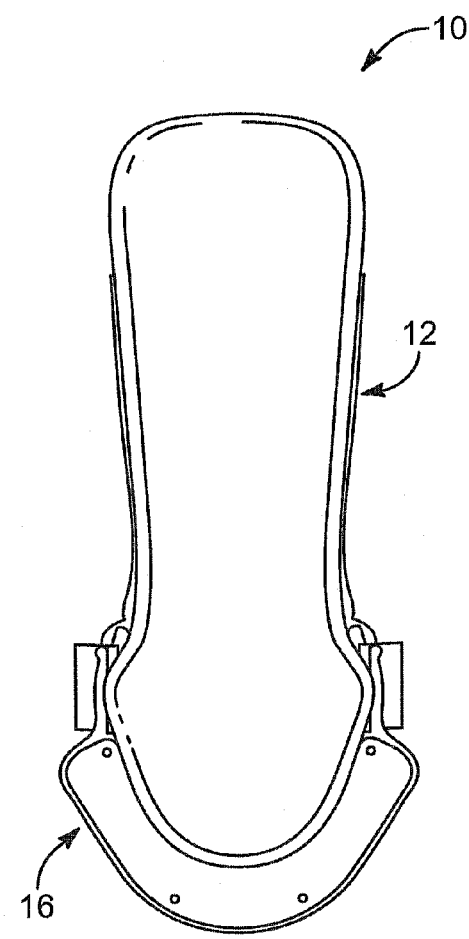
FIG. 17 is a bottom plan view of the apparatus of FIG. 10.

Referring to FIG. 2, while continuing to refer generally to FIGS. 1-9 and FIGS. 10-22, an apparatus 10 in accordance with the invention may include a display 44. The display 44 may be responsible for displaying time, programmatic information for an individual programming the controller 22, as well as status information, instructional readouts, or the like for a user.

The controller 22 may be provided with a port 26 suitable for connecting the controller 22 to a computer, keyboard, or other user interface device suitable for programming the controller 22 for its functional regimen. For example, a doctor may prescribe a particular regimen, which regimen may be programmed by software.

The software may reside in the controller 22 itself, or may reside in a computer external thereto. By either a user interface or computer, a programmer, user, doctor, or medical professional may program the operation of the controller 22 as to time, frequency, power, voltage, current, or any combination or subcombination thereof in order to control the sequencing, intensity, frequency, duty cycle, and the like of the sources 20 controlled by the controller 22. Thus, instructions, data, and the like may be exchanged between the controller 22 and a remote device such as a computer by suitable connection through a port 46.

In general, the port 46 may be of any suitable type, including proprietary or standardized formats. For example, in certain embodiments, the port 46 may be a standard USB port suitable for connecting one computer peripheral device to another, or one computer to another. Accordingly, the port 46 may receive instructions from a remote computer, a user interface, a keyboard, or any other input device, such as a keypad, or unique proprietary device suitable for providing instructions, downloads, or even direct manipulation of the programming of the controller 22.

In general, the sources 20 may be imbedded in apertures made in the struts 14, the base 12, or both. In general, the individual sources 20 may be separately powered and controlled, may be controlled in groups, and individual sources 20 or groups may be controlled in a sequence otherwise manipulated to assure the sequence in which each is properly activated.

The spacing between the sources 20 (e.g., radially therebetween) may be selected according to the electromagnetic flux of any particular coil, the potential for interference, the isolation by sequencing at individual times, or the like. Accordingly, an apparatus 10 in accordance with the invention as illustrated may include more or fewer sources, may include magnetic cores within the sources or air cores, and may include more or fewer of the coils distributed in a particular member, such as a strut 14 or the base 12.

Figure 18:
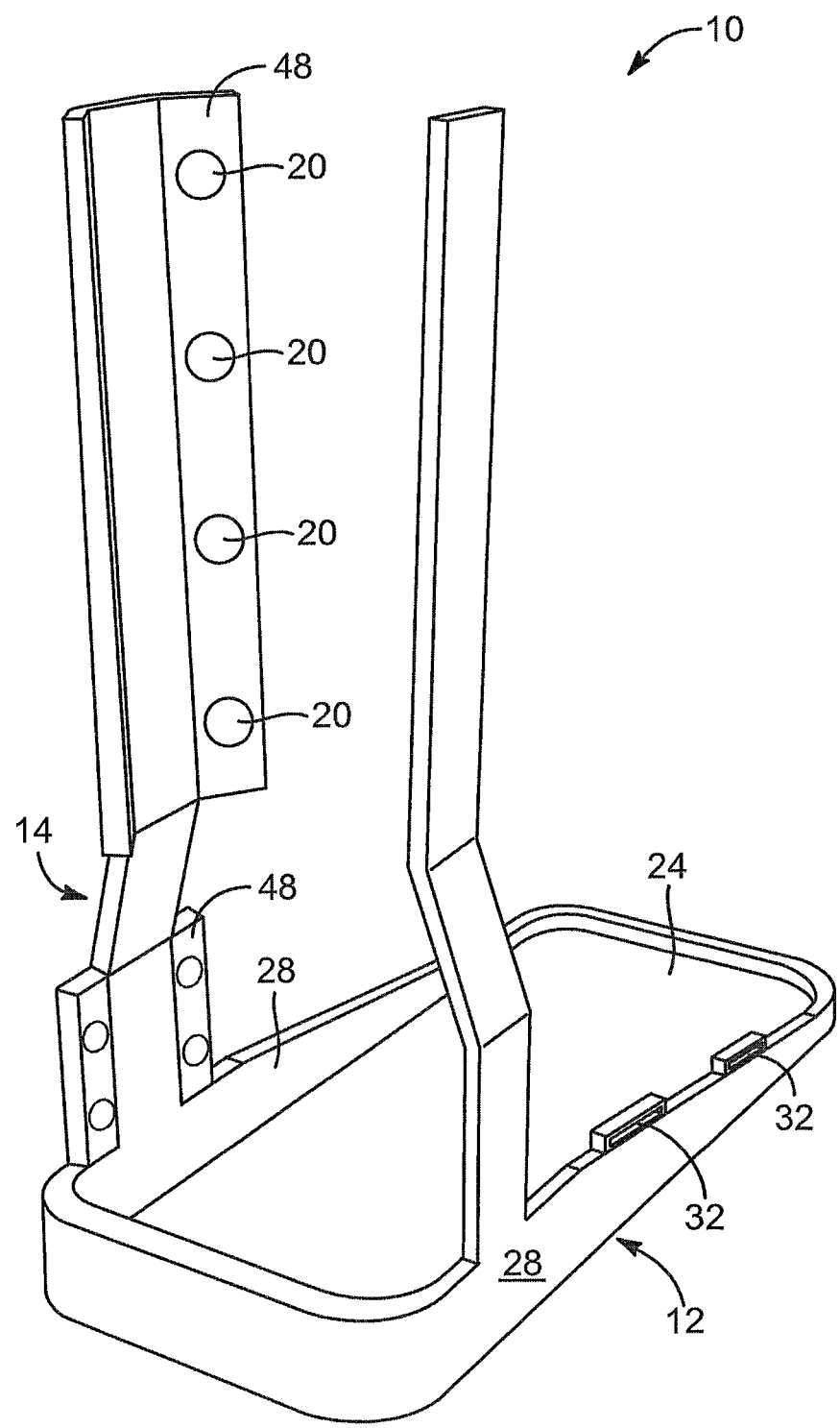
FIG. 18 is a rear upper quarter perspective view of an alternative embodiment of an apparatus in accordance with the invention.

Referring to FIG. 18, a strut 14 of the apparatus 10 in accordance with the invention may include augmentation of a strut 14 by a panel 48. The panel 48 may extend the horizontal domain of the strut 14 to provide additional material and surface area to support sources 20. In the embodiment of FIG. 18, the strut 14 on one side, or the struts 14 on both sides, of the apparatus 10 may be provided with one or more panels 48 containing sources 20. In the illustrated embodiment, the panels corresponding to the nearer strut 14 are removed for clarity in seeing the panels 48 of the opposing side.

As a practical matter, the panels 48 may be formed of a suitable polymer, such as an elastomer, a hard or a flexible plastic, a fiber-reenforced polymer, or the like. Likewise, in order to accommodate the shape and size of a foot, along with the appropriate pad 18 wrapped therearound, the panels 48 may have distinctive shapes suitable for surrounding a member and appropriate to each.

For example, the upper panel 48 is effectively wrapped around the leg of the user, whereas the lower panel 48 may wrap or instead be aligned substantially parallel with the wall 28 of the base 12. The sources 20 may be formed of coils arrayed on front and back portions (with respect to a direction of motion) of panels 48 affixed to the struts 14.

Meanwhile, the bed 24 on which the foot of a user rests may be constructed of multiple layers in order to provide a top witness layer above a lower cushion or other substrate. Thus, the substrate remains whether or not the upper witness layer is compromised. By being compromised is meant that the witness layer may be worn, torn, cut, abraided, or otherwise rendered broken or removed in order that a complementary color of the underlying substrate be visible. The visible underlaying substrate indicates that a user has put pressure, load, or wear on the witness layer, thus violating prescriptive restrictions on motion and on weighting the leg, foot, or the like prematurely.

Figure 19:
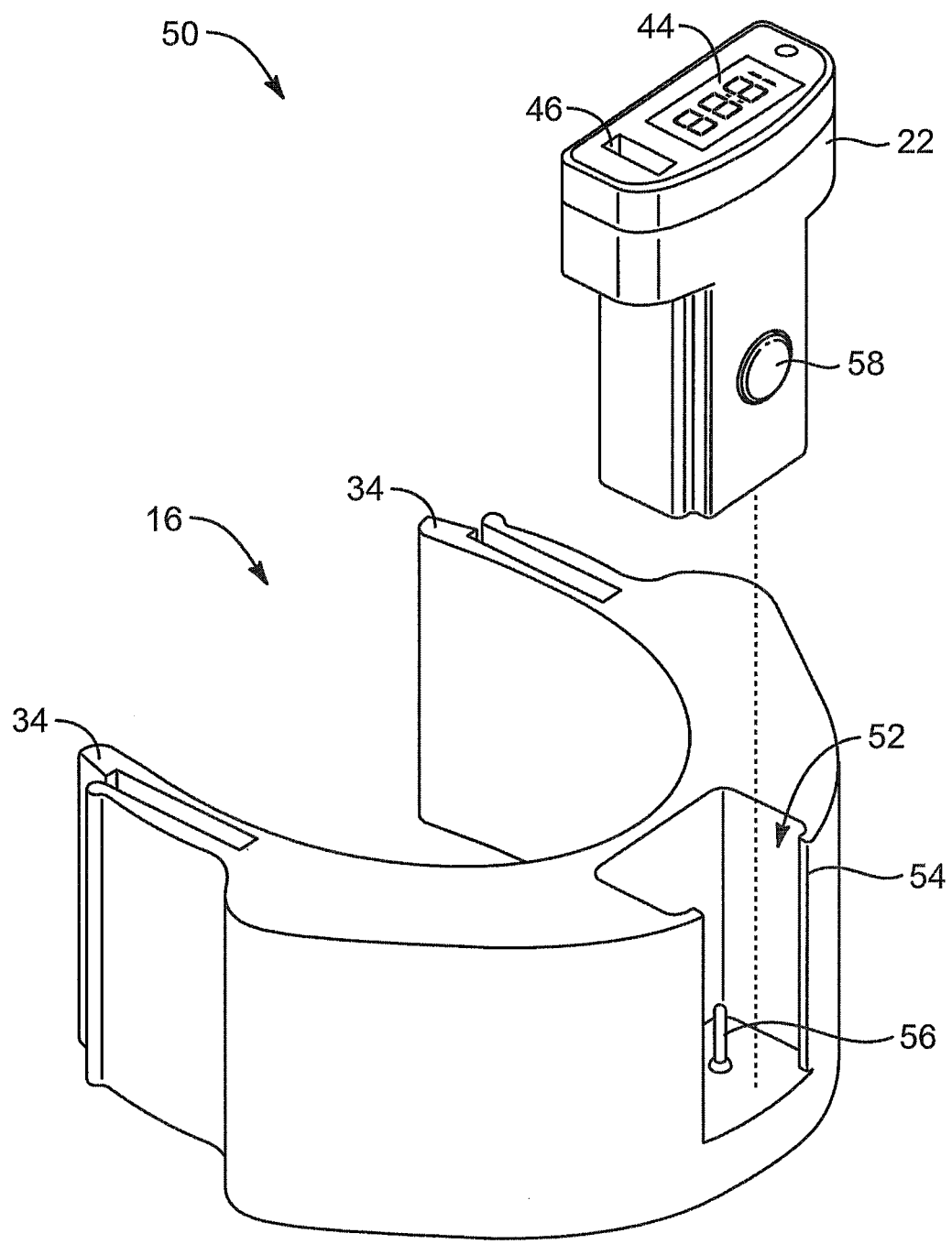
FIG. 19 is a rear quarter perspective view with the controller remove from the battery pack portion of the apparatus of FIGS. 10-17.

Referring to FIG. 19, a module 50 suitable for mounting a controller 22 to the struts 14 of an apparatus 10 may include a receiver 52 formed to matingly receive a controller 22. Typically, a retainer 54 may form a part of the receiver 52, or part of the structure corresponding thereto in receiving and retaining the controller 22 thereby.

In the illustrated embodiment, connectors 56 are received into the controller 22 or controller module 22, making electrical contact required by the controller 22 from power sources within the module 50.

In certain embodiments of an apparatus and method in accordance with the invention, an indicator 58, an operating button 58, or a combination thereof 58 may be provided on or near an exterior surface of the controller 22. For example, an individual may touch the button 58, causing the button to light, beep, or otherwise indicate as an indicator 58. Thus, the button 58 may serve as a button 58 or actuator 58, as well as an indicator 58.

The fasteners 32 may capture the strut 14 in order to secure the module 50 thereto. Suitable embodiments may include one or more of screws, detents, bosses, clips, slides, and other forms of resistance to relative motion therebetween. In certain embodiments, the mere friction maintained by the fastener 34 against the struts 14 may provide vertical support while brackets, barbs, edges, and other forms of capture mechanisms may provide horizontal stability capturing the struts 14 within the modules 50.

A port 46 may be of any suitable type. Proprietary formats may serve well. Nevertheless, inasmuch as many standardized formats have been developed over decades, selection of a suitable format commonly used such as a USB, a mini-USB, or other port 46 may provide electronic data access to the controller 22 by an external programming device, keyboard, computer, or the like.

Meanwhile, the display 44 may be of any suitable type including LED's (light-emitting diodes), liquid crystal display (LCD), Nixie lights or any other suitable format of device for displaying to the user information output by the controller, inputs received, or other graphically or alphanumerically displayed characters.

Figure 20:
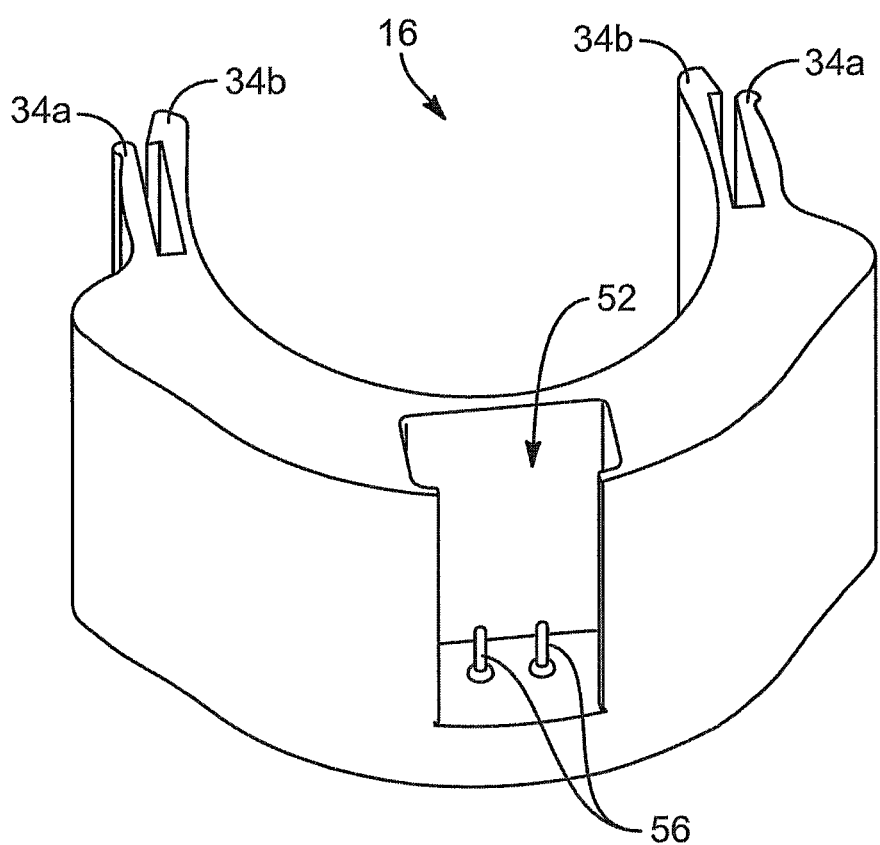
FIG. 20 is a rear perspective view of the apparatus of FIG. 19.

Referring to FIG. 20, the rack 16 may include any suitable number of connectors 56 as appropriate to transmit power, data, or both. Dedicated channels may be supported better by use of more than two connectors 56. Nevertheless, some connectors 56 may provide multiple electrical connections on a single mechanical connector. By whatever mode, the connectors 56 provide communication between the power supply and the controller in the apparatus 10.

Figure 21:
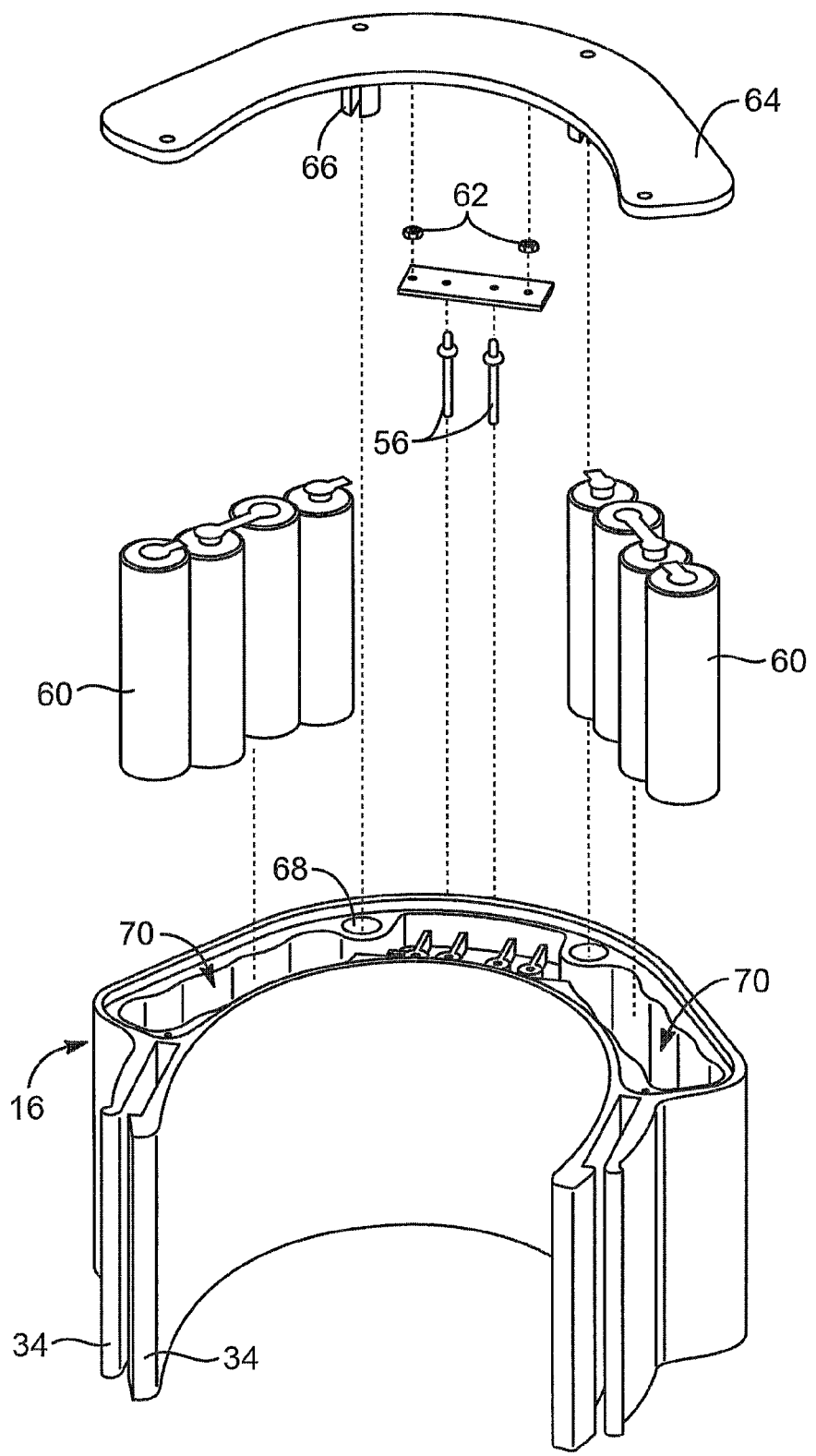
FIG. 21 is a front perspective exploded view of the apparatus of FIG. 19, in an upside down configuration in order to show the bottom plate and battery packs as well as connectors.

Referring to FIG. 21, the rack 16, in an exploded view may be seen to contain a power source 60. The power supply may use line power, rectified DC current, or stored power such as batteries 60, or a battery pack 60 comprising one or more batteries.

In certain embodiments, the power source 60 may be distributed along two sides of the rack 16, in order to reduce the profile of the apparatus 10. For example, at some point, when a patient is ambulatory or walking in a "walking cast" apparatus 10, extension of the rack 16 laterally between the feet or ankles of a user may cause an obstruction to walking.

In the illustrated embodiment, the connectors 56 are secured in the rack 16 by a set of retainers 62. In general, the retainer 62 may be of any suitable type and provide mechanical securement of the connectors 56 for support purposes. The connectors 56 may be connected electrically to wires by soldering, fastening with screws, or the like.

A base plate 64 may secure to the rack 16 maintaining a snug and immovable fit of the batteries 60 or power source 60 within the rack 16. Pins 66 or receivers 66 for accepting screws or other fasteners may penetrate into apertures 68 in the rack 16. Accordingly, fasteners, such as screws, rivets, glue, solvent, latches, and the like may be used to hold the pins 66 inside the apertures 68 without moving appreciably. Accordingly, the base plate 64 may be secured against the rack 16 to store the power supplies 60 or power sources 60 such as battery packs 60 within the rack 16.

The cavities 70 for receiving the power sources 60 or batteries 60 may be suitably shaped to maintain the mechanical relationship between individual elements, such as batteries 60. For example, typical batteries 60 have substantial weight and substantially higher density than many other materials. Accordingly, the batteries 60 may beneficially be maintained separate from one another in order to not provide noise, not damage one another, not damage the rack 16, and so forth. Accordingly, the cavities 70 may be shaped to maintain the batteries 60 each in its particular location, stabilized in up to three dimensions of space.

An additional benefit of forming the cavities 70 about the power source 60 according to the shape of the power source 60, may also include structural efficiency. For example, by providing greater thicknesses and other dimensions of material in the rack 16 where convenient, while thinning down or reducing the amount of material in other places, the overall strength, stiffness, section modules, or the like may be optimized while minimizing distortion and weight.

Figure 22:
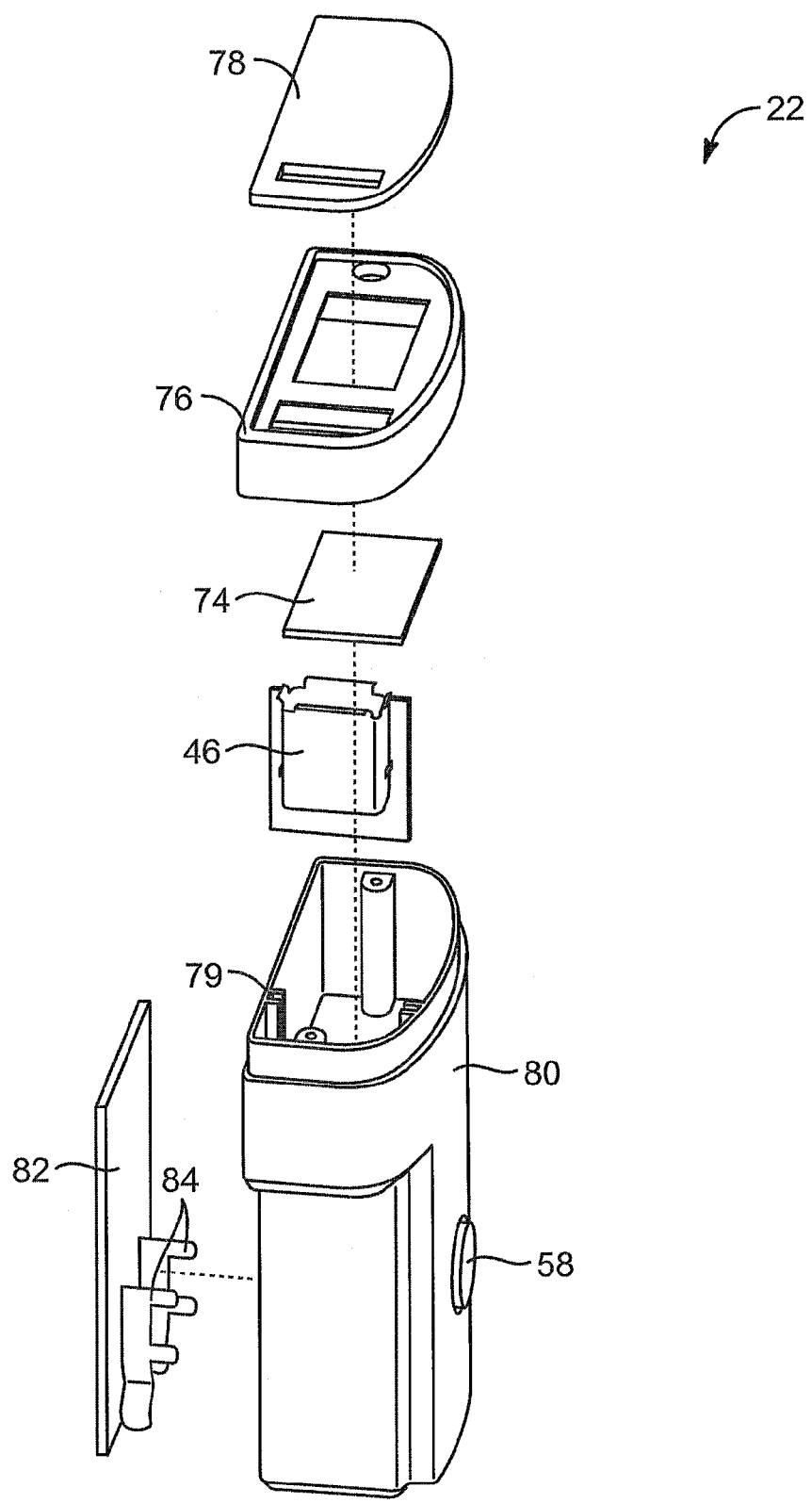
FIG. 22 is a side quarter perspective exploded view of the controller of the apparatus of FIG. 19, as implemented in the apparatus of FIGS. 10-17.

Referring to FIG. 22, the controller 22 may include a readout 74 providing actual display of alphanumeric, graphical, or other indications to a user. The readout may be mounted in a suitable frame 76 or cap 76 suitable for maintaining structural integrity. For example, a display 74 or readout 74 may typically not be particularly robust mechanically. Thus, the readout 74 may actually need the mechanical protection and rigidity provided by the frame 76 or cap 76. Meanwhile, a lens 78 may alter the color, provide glare protection, or otherwise protect the readout 74 mechanically from damage.

The lens 78 may be secured outside or inside the frame 76 in order to provide a suitable securement process. For example, the lens 78 may actually be glued, screwed, riveted, ultrasonically welded or otherwise bound to the cap 76 or frame 76 in a suitable manner. An aperture in the lense 78 may provide access to the port 46.

A port 46 may be mounted on a suitable back plate 47 or other structural member fitted into a bracket 79 in the case 80 suitable for receiving the back plate 47 of the port 46. In the illustrated embodiment, the cap 76 or frame 76 is provided with countersunk holes for receiving a fastener such as a screw that then penetrates into matching apertures within the case 80. Thus, the cap 76 secures together the readout 74, the cap 76 or frame 76, and the port 46 all within the case 80.

The circuit board 82 may be fitted to the back of the case 80 or may be slid into the bottom or the top of the case 80 in any suitable manner to provide suitable data and power connections. For example, the board 82 may be provided with contacts 84 suitable for making a mechanical and electrical connection with the connectors 56 from the rack 16. Thus, whenever the contacts or connectors 56 from the rack penetrate into the case 80, they are aligned with apertures (not shown) accessing the contacts 84 on the board 82. Thus, the connectors 56 penetrate into the case 80 to make contact with the contacts 84 delivering power to the board 82.

Figure 23:
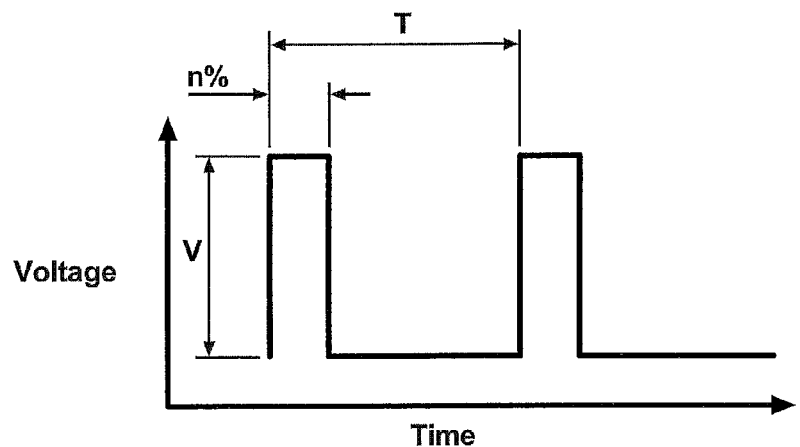
FIG. 23 is a chart of voltage with respect to time to illustrate a reduced duty cycle in the electromagnetic coils in accordance with the invention.

Referring to FIG. 23, the controller may provide to the sources 20 a voltage and current suitable for inducing a magnetic field. Accordingly, each of the sources 20 may include a coil having any suitable number of turns and any suitable material. For example, the sources 20 may include 5, 10, 20, or any suitable number of turns about an air core or a metal (e.g., ferro-magnetic core). Accordingly, FIG. 23 illustrates a typical mode of control relying on controlling voltage applied to a source 20 of electromagnetic force or electromagnetic flux. In the illustrated embodiment, the peak voltage is indicated by the letter 'V' with a total elapsed time indicated by 'T.'

The actual wave form, including rise time and rate and decay time and rate of the voltage may be configured in any suitable manner. For example, in some embodiments, the rise time of the voltage may occur so comparatively quickly as to appear to generate a square wave. Nevertheless, even a square wave has a rise time limitation that actually does not produce the maximum voltage within zero time, but during some comparatively longer or shorter time period.

Accordingly, the wave shape of the voltage may be altered as to its rise time and its decay time in accordance with suitable therapeutic determinations. At this point, it is not considered critical exactly how the rise time and the wave shape are configured. In order to influence the piezoelectric properties of bone material, what is needed is an induced voltage or current within the cells of the body in order to provide a microexercise operating at a substantially cellular level in the bone.

The duty cycle is illustrated by the indicator 'n' in the illustration. For example any particular fraction or percentage of the total elapsed time may be filled with voltage cycles as selected for the time of the duty cycle or the dwell time during which the actual voltage of the illustrated wave form is applied. A series of voltage waves oscillating between the maximum and minimum values may occur at a selected frequency during 'n%' of an elapsed time 'T.' Thus, the 'n%' of the cycle time 'T' (one "duty cycle") defines a period of application of voltage waves, themselves cycling at a selected frequency (typically between 50 and 500 Hertz and usually between 150 and 200 Hertz). Meanwhile, each period 'T' may be repeated during a percentage of the total time of another therapeutic duty cycle. Thus, for example, a voltage may cycle at 150 Hertz for 6 seconds of every minute, repeated five minutes, all repeated once every hour. Thus applied in 24 hours are twelve minutes of voltage cycling. A typical duty cycle may be from about 0.003 to about 0.1.

Figure 24:
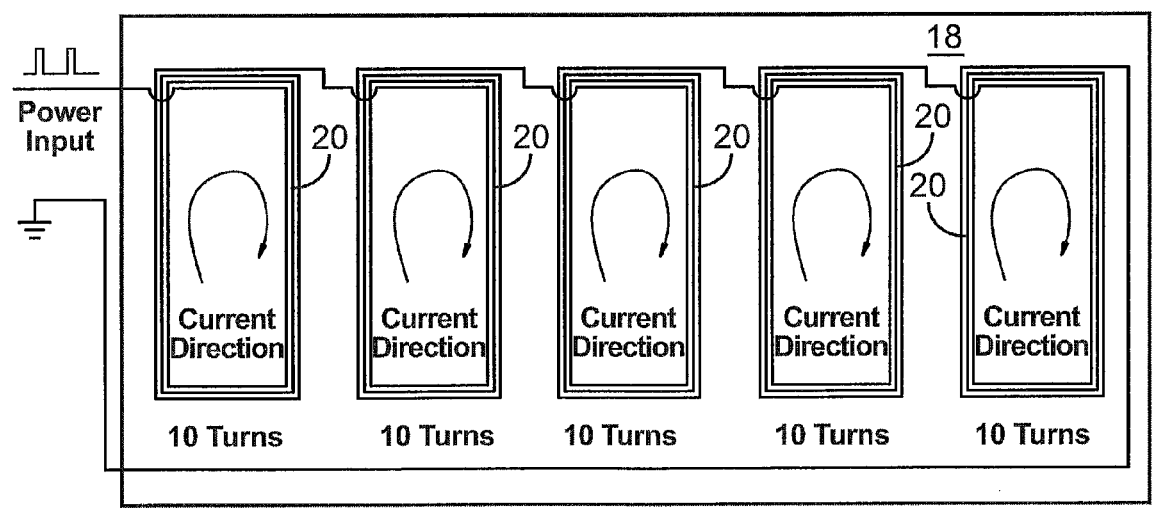
FIG. 24 is a schematic diagram of one embodiment of a wrap having a series of coils sequenced along extent thereof.

Referring to FIG. 24, in one arrangement, a series of sources 20 or coils 20 may be connected to be actuated together. For example, each individual source 20 or coil 20 must receive power from someplace. Whenever a current is run, it may be run through any suitable number of sources 20 in series. In order to sequence the actuation of these individual series of sources, different series of coils 20 or sources 20 may be connected separately. Each particular series may be actuated upon its particular circuit receiving voltage (or current, but actually both, since they occur together).

In the illustrated embodiment, five separate coils 20 are connected in series, such that the voltage across the entire series is the controlled voltage. Accordingly, inasmuch as the five coils are identical and arranged in series, each has its proportionate share of the applied voltage. Meanwhile, each is provided the same number of turns, ten in this instance, and each of the five coils 20 may provide one fifth of the overall voltage drop applied to the series.

Meanwhile, being connected in series, each of the coils 20 of FIG. 24 receives the same current. The current applied by the power supply must travel through all of the coils 20 in order to travel through any of them. Thus, for example, the voltage trace or wave form may be applied to the series of coils 20 in FIG. 24 as the voltage or power input. In reality, a power input will provide a voltage and a current. Thus, application of either voltage or current will necessarily carry with it the other of these two parameters in order to constitute power used by the apparatus 10.

Referring to FIG. 25, testing results for one embodiment of an apparatus and method in accordance with the invention applied various voltages ranging from six to 24 volts as illustrated in the first column of FIG. 25. Initially, a frequency of 500 Hz in which 'n' the duty cycle in percentage was five percent. Thus, voltage at 500 Hertz was applied five percent of the total elapsed time 'T.'

It should be understood that the duty cycle may be controlled in multiple ways. In certain embodiments, the individual coils 20 may be activated during some overall period of time during which the duty cycle percentage or 'n' is a time period in which an alternating voltage is applied. Meanwhile, the elapsed time 'T' may itself be repeated at some particular periodicity. Thus, another overall time may represent the amount of time during which several individual periods (T) are applied.

Likewise, a voltage may be applied (rise) and decayed hundreds of times per second. With one cycle per second being a single Hertz, a voltage may be applied and dropped once in a single cycle time 'T'. Thus, a voltage rise may occur and disappear, followed by a lengthy period of no electrical activity. In another embodiment, the voltage may be applied and decayed multiple times during the portion 'n' of a cycle time 'T'. Thus, the cycle time 'T' may represent a single cycle time of application of voltage, or the cycle time 'T' may be an application of voltage hundreds or thousands of times as alternating voltage at a frequency during the fraction n or percentage n of an overall time period 'T.'

Then 'T' may be repeated several times during every larger time period $T_1$, which may be repeated several times in a larger time period $T_2$, and so forth.

Referring to FIG. 25, the voltage applied ranged from six volts to 24 volts. Meanwhile, the frequency or the number of Hertz was held at 500 Hertz for the first experiment, 500 Hertz for the second experiment, and 200 Hertz for the third experiment. Meanwhile, the duty cycle or the percentage 'n' of the time that the voltage was so alternating for each time period 'T' ranged from five percent for the first experiment to ten percent for the second experiment and five percent for the third experiment.

The magnetic flux densities in micro Tesla are shown. Average currents in Amperes were likewise as shown. One will note that, for example, at six volts using a 500 Hertz signal with a five percent duty cycle, the magnetic flux density is 7.4 micro Tesla. Meanwhile, for the same frequency with a ten percent duty cycle, the magnetic flux density is 15.7 micro Tesla, or more than twice the magnetic flux density. Meanwhile, at 200 Hertz, the six volt power supply provides a magnetic flux density of nine micro Tesla even at a five percent duty cycle.

Meanwhile, at 16 volts, the 500 Hertz experiment with the five percent duty cycle produced 18 micro Tesla while the 500 Hertz experiment at ten percent duty cycle produced a 26.8 micro Tesla result. No longer is the flux density double for the greater duty cycle. Meanwhile at 200 Hertz, using a five percent duty cycle, the 16 volt experiment produced 14.6 micro Tesla. Thus, the flux density is less than that of the 500 Hertz and five percent duty cycle experiment, whereas at six volts, the 200 Hertz and five percent duty cycle experiment had greater magnetic flux density than the 500 Hertz and five percent duty cycle experiment.

Thus, it can be seen that the flux density, and the use of power may be optimized for any particular set of sources 20. Accordingly, the size of the aperture or core space in each source 20 may be selected and matched to a particular voltage and current to be run through the source 20 as well as the number of sources 20 or coils 20 to be placed in a particular series.

Figure 26:
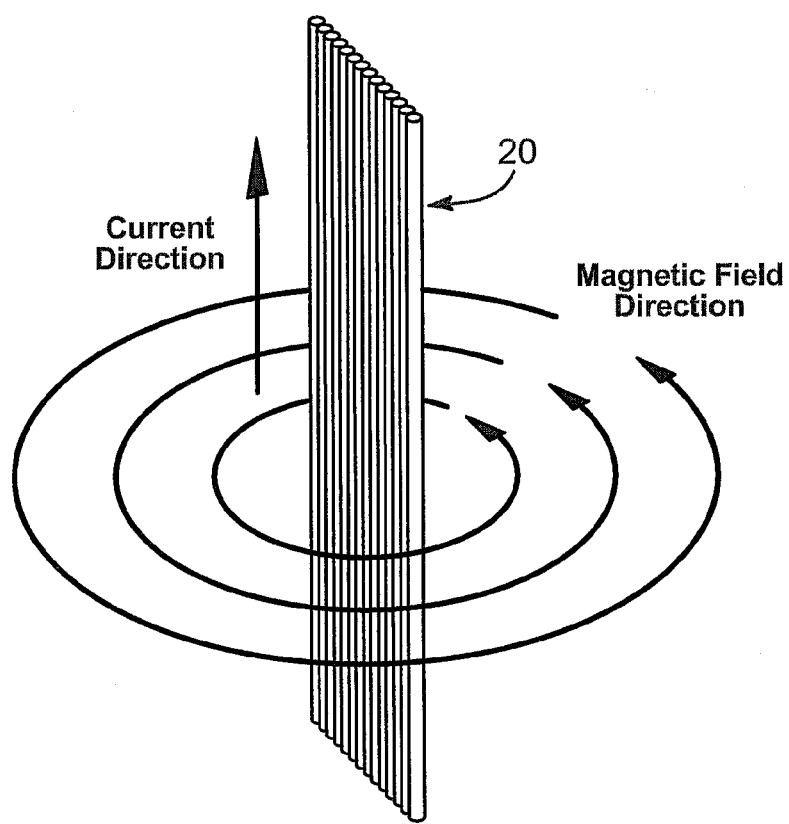
FIG. 26 is a schematic diagram illustrating the current direction for the wires of a coil with the corresponding direction of the magnetic field generated thereby.
Figure 27:
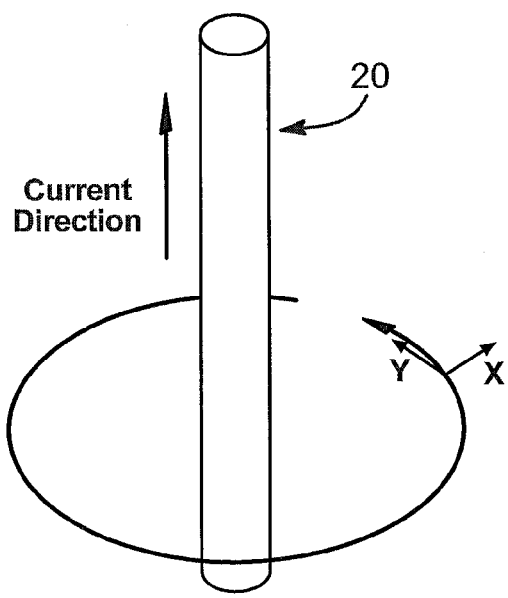
FIG. 27 is a schematic diagram illustrating the current direction in a conductor with the resulting direction of the magnetic field induced thereby.
Figure 33:
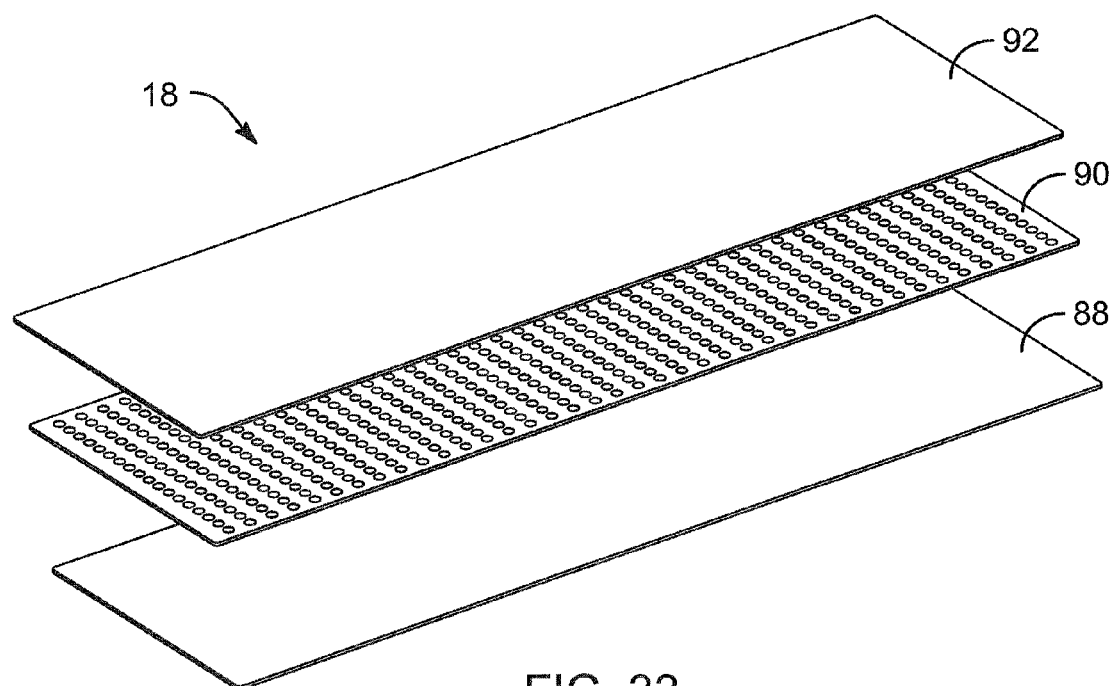
FIG. 33 is an exploded view of one embodiment of a wrap or pad material for use in an assembly in accordance with the invention, illustrating covering layers, enclosing or capturing a layer holding embedded electromagnets therein.
Figure 34:
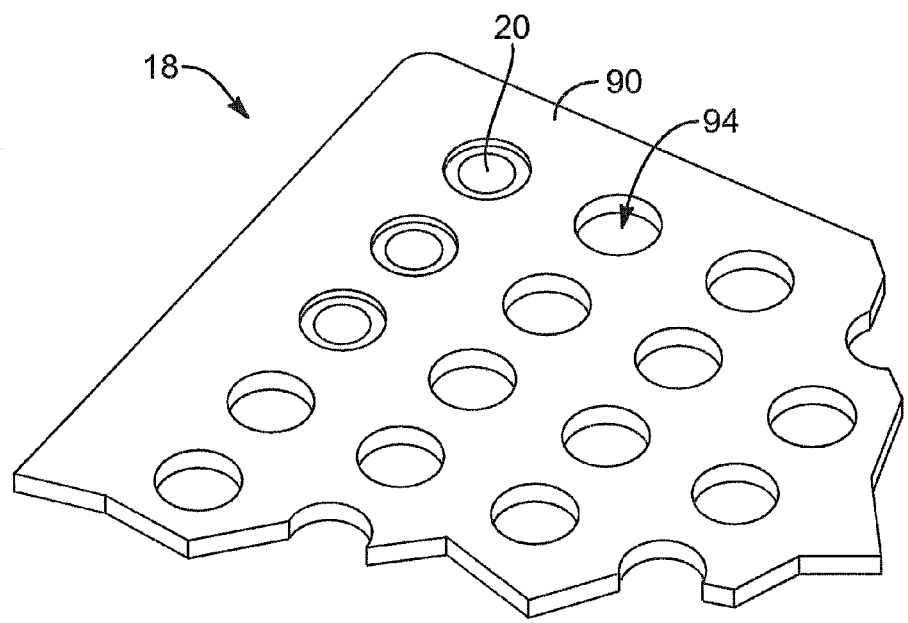
FIG. 34 is a partial, cutaway, perspective view of one embodiment of the inner mat from the apparatus of FIG. 33.
Figure 35A:
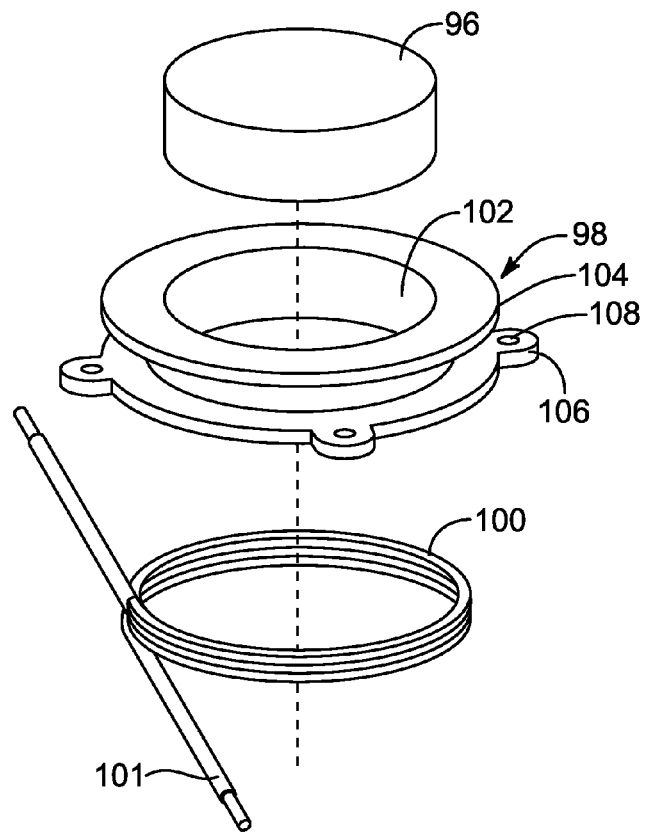
FIG. 35A is a perspective, exploded view of one embodiment of an electromagnet for use in an apparatus in accordance with the invention such as the mat of FIGS. 33-34.
Figure 35B:
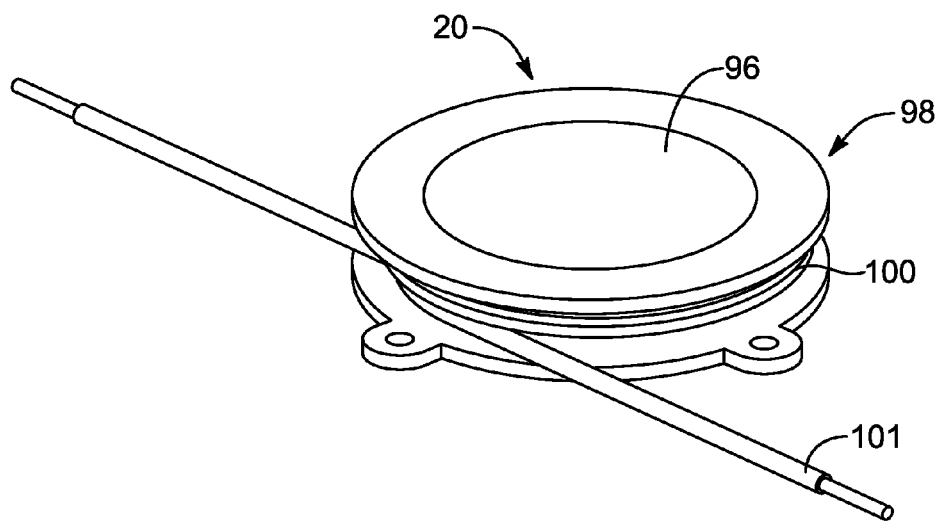
FIG. 35B is a perspective view of the assembled electromagnetic coil with optional magnetic core shown for the apparatus of FIG. 35A.

Referring to FIGS. 26 and 27, the laws of electromagnetics indicate that the magnetic field surrounding a conductor having a current flowing in a first direction abides by the "right-hand rule." The right-hand rule states that if the thumb of the right hand is facing in the direction of current along a conductor, with the fingers of the right hand wrapped around the conductor, then the direction of the magnetic field is the direction of the fingers of the right hand wrapped around the conductor. Thus, in FIG. 26, the conductor current direction applies to all of the turns within a particular coil 20. Nevertheless, recall that a source 20 may include more than a coil. The coil 20 may contain an air core, in which the coil 20 is the entire source 20 or may contain a magnetic core in order to better control, develop, and direct the magnetic flux through the coil 20.

Likewise, FIG. 27 illustrates a conductor, having a current direction, and a magnetic field direction. At locations nearest a coil, the magnetic flux may crowd and curve around the conductor by the right hand rule. Some distance away from the center thereof, the flux lines may distribute more widely. Accordingly, magnetic flux lines may be defined directionally with respect to the conductor, in all three dimensions, as they propagate through space in their particular geometry.

Referring to FIG. 28, testing results for an experiment ranging from six volts to 24 volts with a 150 Hertz frequency and a five percent duty cycle illustrate magnetic flux densities in micro Tesla along the x axis of FIG. 27, the z axis thereof, and the y axis thereof. X, Y, and Z are mutually orthogonal. Accordingly, in the illustration of FIG. 27, the current direction is the Z direction. Meanwhile, the X direction is the direction radially outward from the conductor, while the Y direction is the circumferential direction around the conductor.

One will note that the magnetic flux density in a radial direction X compares with the flux density in the circumferential or Y direction. Meanwhile, the magnetic flux density along the Z direction of the conductor or current flow direction is typically an order of magnitude or more less than that in either of the other directions, which flux densities are typically comparative.

Referring to FIG. 29, the 150 Hertz experiment was duplicated through the voltage range from six volts to 24 volts as illustrated, with magnetic flux densities calculated in the X, Y, and Z directions or along those axes. Substantial increases in flux densities along the X and Y axes are apparent and, although smaller, increases are also shown along the Z axis.

Referring to FIG. 30, the testing results for an experiment at 500 Hertz and a five percent duty cycle illustrate substantially reduced magnetic flux densities in the X and Y directions, with about the same proportion of flux density distributed to the Z direction. This experiment ranging between six volts and 24 volts also illustrates that the average current Amperage is substantially reduced at this high frequency compared to the current at the lower 150 Hertz frequency. Although the five and 10 percent duty cycles of FIGS. 28 and 29, respectively, are at least within the same order of magnitude of one another, the increase to 500 Hertz shows a dramatic decrease, in response to the slower inductive properties of magnets at increased frequencies.

Referring to FIG. 31, the 500 Hertz experiment is repeated at a ten percent duty cycle, showing marked increases in the magnetic flux densities along the X and Y axes, with about the same proportional response in the Z direction as well. Typical current also increases, to approximately double that of the 500 Hertz and five percent duty cycle experiment.

Referring to FIG. 32, the testing results from a 200 Hertz experiment and a five percent duty cycle in the range of voltages from six to 24 volts shows a magnetic flux density comparable to the 150 Hertz five percent duty cycle. Accordingly, the voltage, the frequency, the duty cycle may be manipulated to provide the appropriate therapeutically effective magnetic flux density and dwell time or duty cycle desired.

Specific values of parameters such as frequency and flux densities have been found to trigger somewhat distinctive specific responses in different tissue types. For example, a specific frequency and micro Tesla ratings have been found to significantly increase the healing of skin and open wounds, whereas other frequencies have been found to relieve inflammation (i. e., reduce swelling and relieve pain). Yet other frequencies stimulate bone growth.

In certain embodiments of an apparatus and method in accordance with the invention, the particular frequencies may be selected to be applied serially, one following another. The applications may be "multiplexed" or divided in time by increments, each defining a time span in which power is applied, followed by the next time period, and so forth. Any part of the foregoing duty cycles discussed above may be so subdivided, whether a single wave function at a time, a period of constant wave oscillation at a time, a series of interrupted applications of a continual wave a time, a duty cycle of any configuration at a time, or an entire treatment regimen at a time for one single frequency, flux density, or the like for one period of time corresponding thereto.

Alternatively, one treatment regimen, appropriate to one tissue type or effect (e.g., relief or pain or swelling, repair of skin damage, etc.) may be run over minutes, hours, days, weeks or any other appropriate time period, at one set of parameter values. Thereafter, another regimen (e.g., repair of muscle trauma, bone healing, bone densification, etc.) may follow with its own set of parameter values. Thus, whether effectively simultaneous or sequential, a particular set of treatment may be programmed and run, each with its own timing and priority.

Thus, several conditions or a single condition of highest priority may be addressed by an apparatus and method in accordance with the invention. Pain relief and bone growth may be sequenced or simultaneous, each as needed and according to the bodily resources' ability to respond to highest priorities with their most effective means to respond.

In certain embodiments, one may combine all desired frequencies at once to promote overall repair and maintenance. In another embodiment, the apparatus and method may cycle through different frequencies during the use period. Meanwhile, different settings for parameters, different periods of application of frequency and flux, and different durations of regimens, as well as distinct starting times hours or days hence may be programmed into an apparatus to implement such a method to meet a particular need. Meanwhile, needs may range through pain reduction, swelling reduction, soft tissue repair, bone fusion, bone density maintenance, epithelial repair, soft tissue maintenance to exercise at a micro level to replicate everyday bodily use, each at the flux density and frequency determined to be most effective for each intended regimen.

Referring to FIGS. 33-36, while continuing to refer generally to FIGS. 33-49, a pad 18 may be arranged with any number of series of sources 20. For example, in the illustrated embodiment, the pad 18 is provided with numerous sources 20 mechanically laid out in an array.

The pad 18 may have an inner portion 88 or inner layer 88 over a center layer 90 or center portion 90, all covered with an outer layer 92. Apertures 94 may be formed to be fitted with sources 20. Each source may be made up of a spool 98 supporting a coil 100 of wire 101. Each spool 98 may be made up of a drum 102 or drum portion 102 flanked on either end thereof by flanges 104 or flange portions 104.

One or more tabs 106 on at least one flange 104 may serve to secure each spool 98 to the center layer 90 to secure the spool 98 with respect thereto. The apertures 108 in the tab 106 may receive therethrough a thread or other fastener. A suitably soft polymer or composite may not require an aperture 106, if a needle us used to simply penetrate some portion of a tab 106, flange 104, or both.

Figure 36:
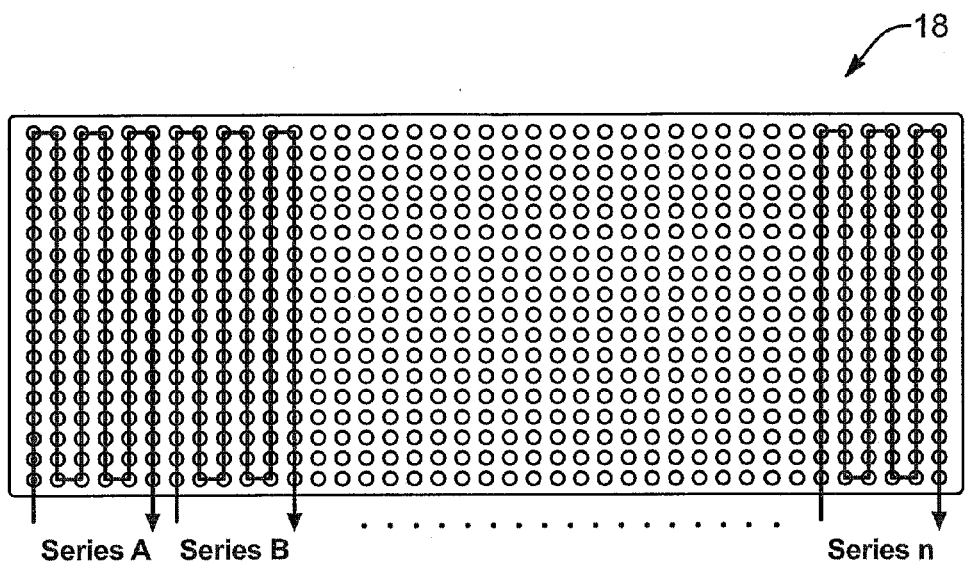
FIG. 36 is a top plan view of one embodiment of a mat, such as the mat of FIG. 34, embedded within the wrap or covering of the apparatus of FIG. 33.

Referring to FIG. 36, while continuing to refer to FIGS. 33-49, various portions of the mechanical array may be electrically connected in various series, such as series A, series B, and so forth up to some number of series that represents the maximum, such as the series n. Each series represents one circuit. Each of the sources 20 in one series will be energized at the same time by a source of voltage, current, or typically both.

Either voltage or current is typically controlled, and the other relies on the response of the circuit. Thus, the number of sources 20, the number of turns in each, the presence or absence of a magnetic core, the wire size, the frequency of application of the current, and the like may control the specific current traveling through each source 20 upon application of a particular voltage.

The pad 90 or the inner layer 90 of the mat 18 may be thermally bonded fabric. Meanwhile, a computerized numerical control may be used to automatically place cores and cut fabric. Meanwhile, various taped strips of coils may also be used to fabricate series of coils suitable for placement within the inner layer 90 of the pad 18.

For example, a pair of layers of synthetic fabric, such as a non-woven fabric formed of a synthetic fiber may travel through a machine laying coils either in the direction of travel of the material, or orthogonal to the direction of travel. Accordingly, computerized equipment may apply pressure and heat at selected locations, such as the center of a coil 20, the periphery of a coil 20, or both. Thus, the fabric may fix and preserve the location of each of the coils or sources 20 with respect to itself.

For example, in one embodiment, a tool may apply a ring of pressure and heat just inside the inner diameter of one of the sources 20. Meanwhile, at the same time, or at another time, a tool may apply a circle of heat around the outer periphery of the coil or source 20. Thus, the source 20 may be completely stabilized within fabric without the need for any spool 98 therewithin.

The thickness of the wire 101 of the coils 100 may be minimized by removing any external insulation layer. For example, magnet wire may be formed to have a flexible enamel on the outer surface thereof, thus providing insulation that is more integral with the wire 101. In this manner, the wire diameter may be very thin, and the inner core 90 of the pad 18 may be particularly flexible and soft, without the need for thick layers of padding in order to obscure the effects primarily of the spool 98 itself.

Of course, the spool 98 may be made small, thin, and so forth, including being made of a very soft elastomeric polymer. Nevertheless, the spool 98 may be dispensed with in favor of stabilizing each of the coils 100 within fabric itself. In fact, in certain embodiments, the entire pad 18 may be bonded periodically by thermal bonding, if made of a synthetic material suitable for bonding by addition of heat and pressure. In this manner, the coils may be stabilized, yet the overall pad 18 may be made comparatively thin or thick according to comfort, rather than being subject to excessive mechanical constraints due to the mechanics of the sources 20 and their optional spools 98.

Figure 37:
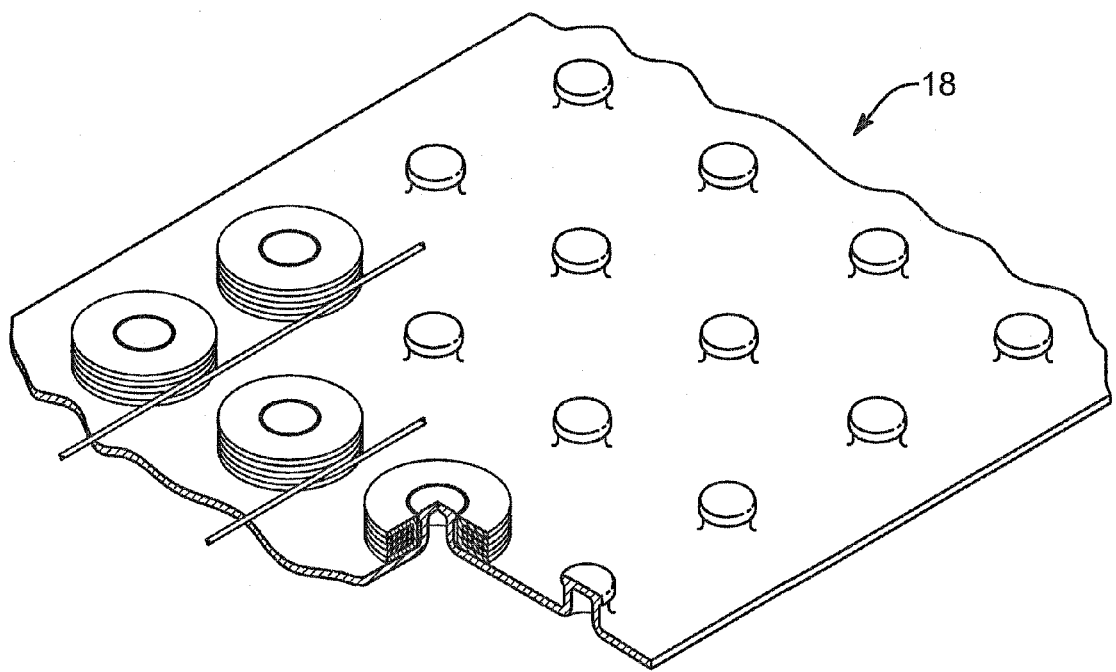
FIG. 37 is an alternative embodiment of the mat of FIGS. 33 and 36 in which the coils may be captured on spools or spindles rather then embedded within a mat, and the core regions may still be provided with metallic centers, or may simply rely on air cores.

Referring to FIG. 37, in one embodiment of an apparatus in accordance with the invention, spools 98 may be secured to a core 90 by a series of pedestals or bollards 109. In the illustrated embodiment, the basic mat 90 or core 90 may be formed of a flexible layer of a polymer, such as an elastomeric solid sheet or layer of expanded foam material. Meanwhile, by vacuum forming, pressing, die stamping, blow molding, or the like, the core 90 may be formed to have small bollards 109 to receive spools 98.

In the illustrated embodiment of FIG. 37, the bollards are provided with a main pedestal and a top keeper that provides a detent to secure spools 98 thereto. Accordingly, spools 98 may be snapped onto the bollards 109 to locate and stabilize each of the coils 100 therearound. Meanwhile, an outer layer 92 may be applied by bonding, heat, or the like at the top of each of the bollards 109 in order to close in the coils 100 and their respective spools 98.

Figure 38:
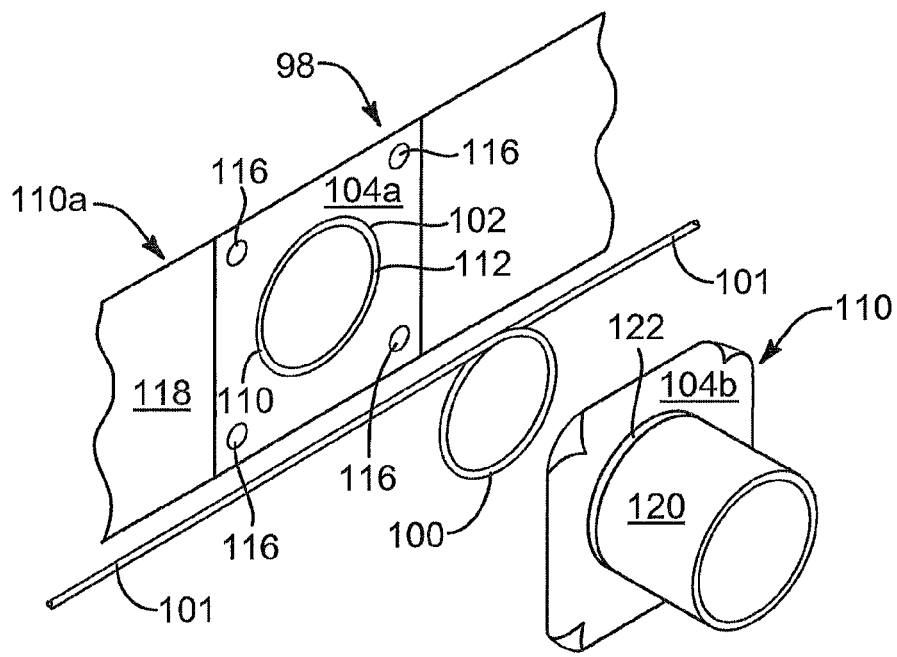
FIG. 38 is an illustration of an alternative embodiment for embedding coils within a synthetic material or a natural material by bonding directly a covering material around the coil, thus capturing the coil in a sandwich of material, which may be bonded by a separate adhesive or by a thermal bond, such as between two layers of synthetic (polymeric) material melted by heat, or the like, and may include nonwoven fabric as the underlying material, the bonded capturing material, or both.

Referring to FIG. 38, in one embodiment, non-woven fabrics may be used, thus reducing costs substantially for the central portion 90 of the pad 18. Nevertheless, woven fabrics may be used as well. However, typically, synthetic fabrics formed of polymers based on petroleum typically have melting temperatures lower than those of natural fibers such as wool, cotton, flax, and the like. Likewise, certain natural fibers will not effectively bond by melting.

Thus, in one embodiment of an apparatus and method in accordance with the invention, a layer 110 of fabric may receive a coil 100 applied thereto. Meanwhile, an anvil behind the layer 110 (not shown) may be heated or may simply provide a resistance to the pressure applied by another tool such as a sealing head 120 or a head 120 providing heat and pressure.

In one embodiment, a layer 110a of fabric 110 may have a coil 110 laid thereagainst, after which, a bonding ring 112 may be formed in the center of the coil 100, around the outside thereof, or both. For example, the core region 114 of the coil 100 may be separated away from the coil 100 by the head 120 applying pressure and heat to the layer 110b of the fabric 110 thus forming the bonding ring 112 of bonded fabric within the inner perimeter of the coil 110.

Accordingly, the spool 98 is actually formed simply by the bonding ring 112 acting as the drum 102 inside the coil 100. Meanwhile, tack welds 116 at strategic locations, or a ring about part or all of the entire periphery outside the coil 100, may bond the layers 110a, 110b together. Thus, the coil 100 is captured and stabilized inside a fabric spool, whose dimensionality is preserved by the fabric 110 itself. Any appropriate number of the coils 100 may be so bonded between layers 110a, 110b, of any extent. In the illustrated embodiment, the layers 110 may be formed into a tape 118. Thus, the layer 110a may be continuous while the layer 110b may be discontinuous patches of the fabric 110. Between any two coils 100 the fabric 110 and wires may be cut and controlling power leads attached to the wires.

By applying a ring or even a complete cylindrically filled plate 122, the bonding ring 120 or the head 120 may form the bonding ring 112. If a magnetic core is to be applied in the core region 114, then such a core may be captured within the bonding ring 112 during the bonding process. The hot plate 122 or hot ring 122 may thus be designed according to whether or not a magnetic core will be captured in the core region 114 or not.

Figure 39:
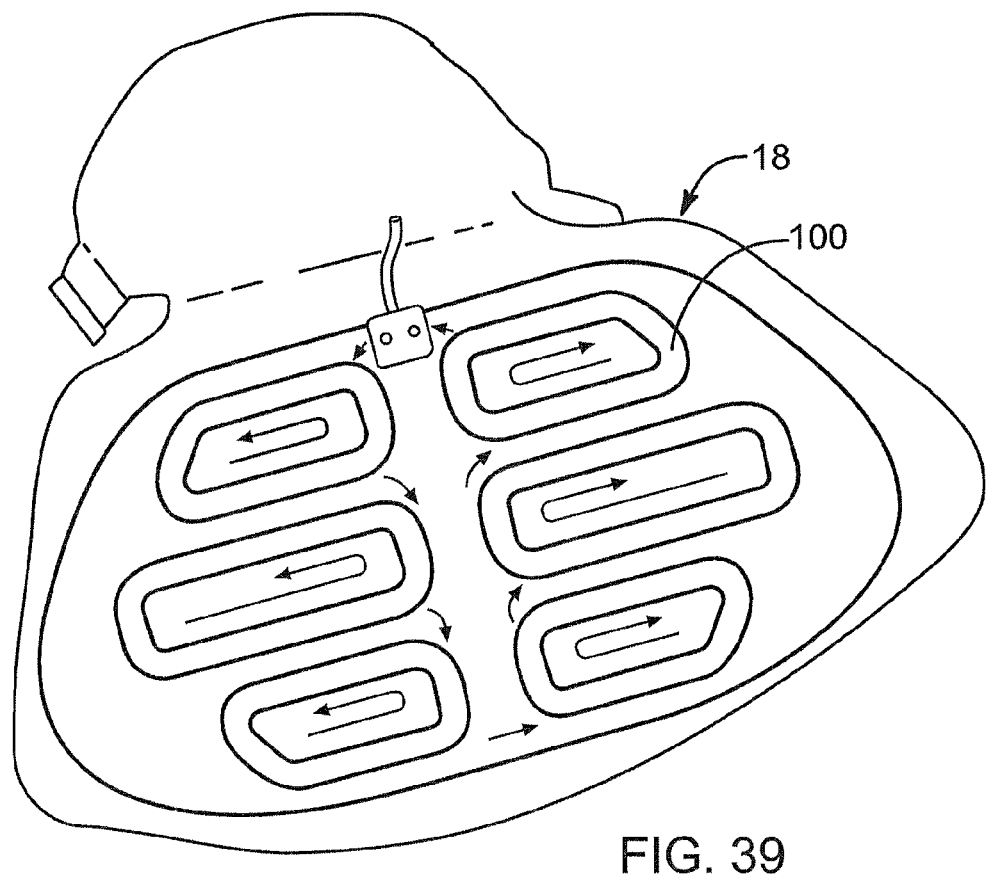
FIG. 39 is a perspective view of an alternative embodiment of a wrap for use in a removable boot cast, and illustrating a plurality of coils embedded within the wrap.

Referring to FIG. 39, in one embodiment of a pad 18, various coils 100 may be bonded by any suitable mechanism. For example, the method of FIG. 38 may be made to have a somewhat sophisticated shape of die representing the function of the hot ring 122. If a head 120 can be made in a suitable shape, then a single application of pressure and temperature along the entire pattern of the pad 18 may stamp the coils into a stable relationship with the pad 18. In alternative embodiments, the coils 100 may actually be printed on a substrate that is then bonded to the pad 18.

Of course, in accordance with previous embodiments discussed hereinabove, the wire coils may be embedded in the pad 18 by thermo-pressure bonding of the fabric materials together, thus capturing the coils therein.

Figure 40:
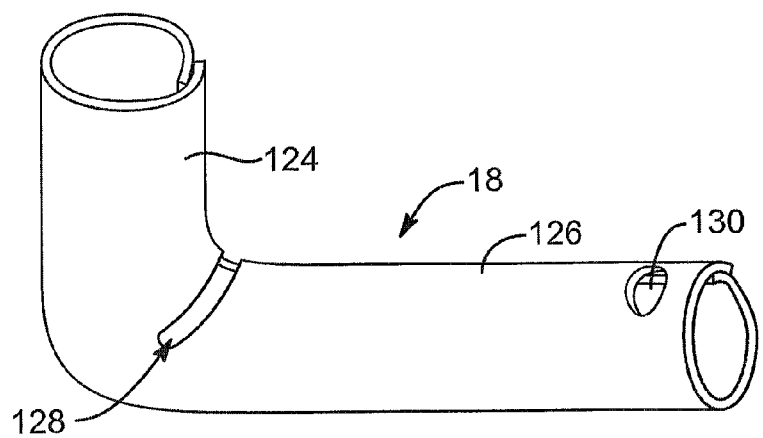
FIG. 40 is a perspective view of one embodiment of a wrap suitable for an arm, and adaptable for use in a splint or removable cast frame, or even included within a cast or the outside of a cast in order to provide the coils in accordance with the invention.
Figure 41:
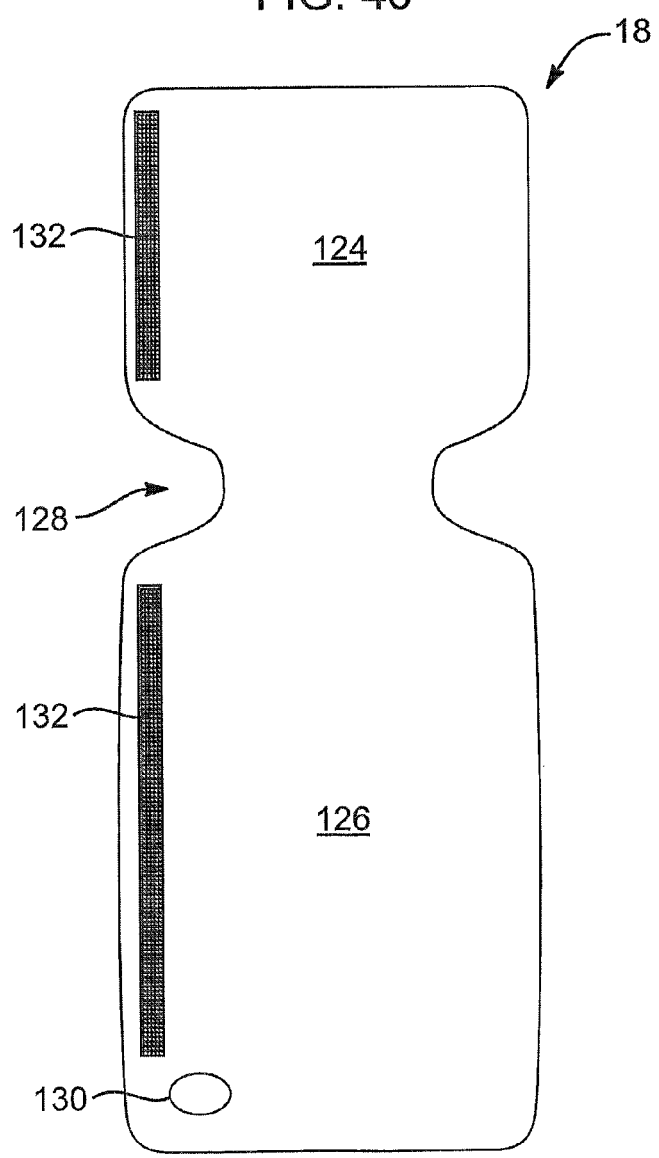
FIG. 41 is a plan view of the wrap or cover of FIG. 40 unwrapped and showing the removable hook and loop fastener or other fastener material.

Referring to FIGS. 40-41, one embodiment of a pad 18 suitable for use around or within an arm splint or cast may include an upper arm portion 124 connected to a lower arm portion 126. A gap 128 may be provided in order to provide relief for closure at the inside surface of an elbow of a user. In one embodiment, an aperture 130 may be required for a thumb. Nevertheless, in some embodiments, the cast may terminate at the wrist in order to immobilize an elbow, without necessarily requiring immobility of a hand.

Various types of fasteners 132, such as hook-and-loop fasteners, may provide securement of the pad 18 to itself. For example, the upper arm portion 124 may wrap around the upper arm of a user, being secured to itself by a fastener 132, such as a fastener strip 132. Likewise, after bending, the lower arm portion 126 may then be formed to wrap against itself by suitable fasteners 132, such as a fasteners strip 132 or other fastener mechanism as appropriate.

Figure 42:
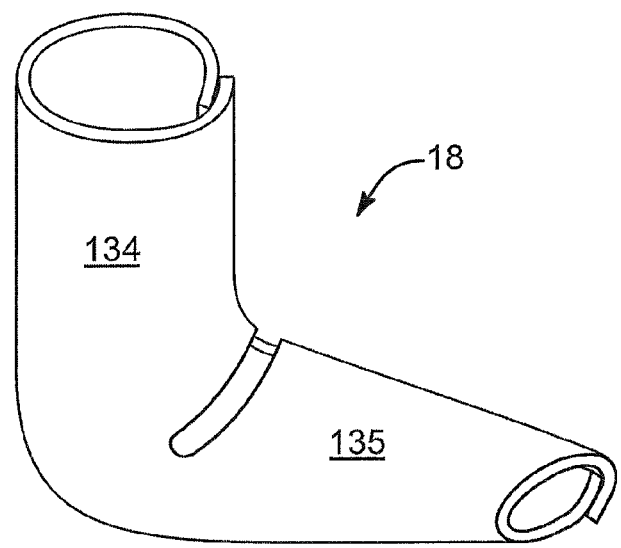
FIG. 42 is a perspective view of one embodiment of a wrap suitable for a boot cast in accordance with the invention.
Figure 43:
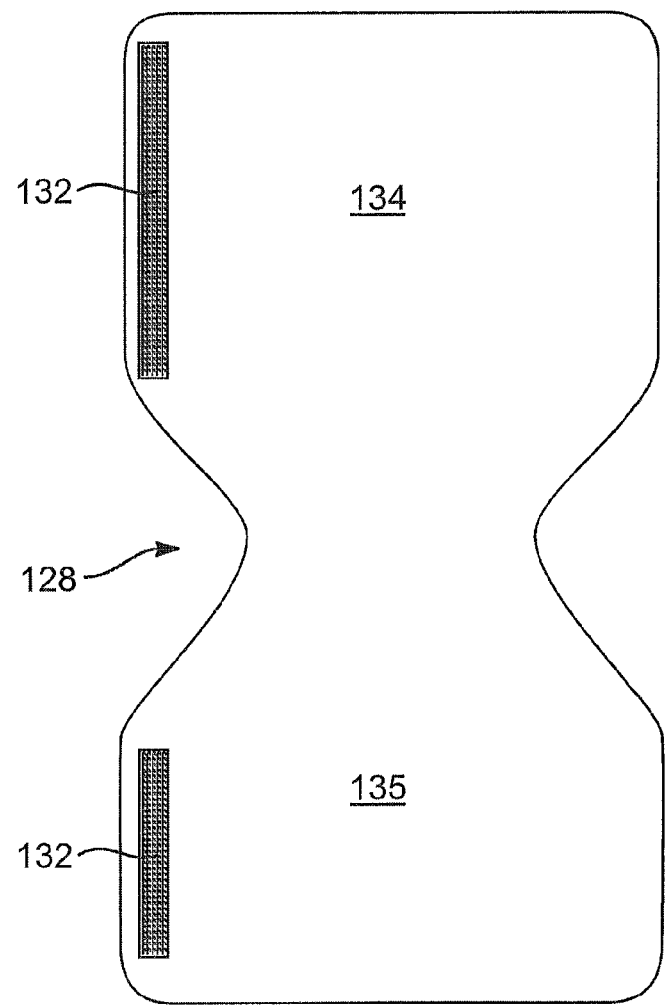
FIG. 43 is a plan view of an unwrapped cover or wrap of FIG. 42 as it may appear before being assembled around a foot.

Referring to FIGS. 42-43, a wrap 18 or pad 18 suitable for use on a foot, leg, or both of a user may include a leg portion 134 and a foot portion 136. The leg portion 134 and foot portion 136 may be formed of a single piece of material having a suitable gap portion 128 in order to relieve the bunching of extra material at the inside of the bend formed therein upon application to a user. In the illustrated embodiment, as in the embodiment of FIGS. 40-41, the pad 18 may be a pad 18 in accordance with the invention having a number of sources 20 having coils 100 arrayed in any suitable format for applying electromagnetic flux to the foot, to the ankle, to the leg, or any combination thereof. The pads 18 may contain a splint (not shown), be used with a cast 10 system, or the like.

Figure 44:
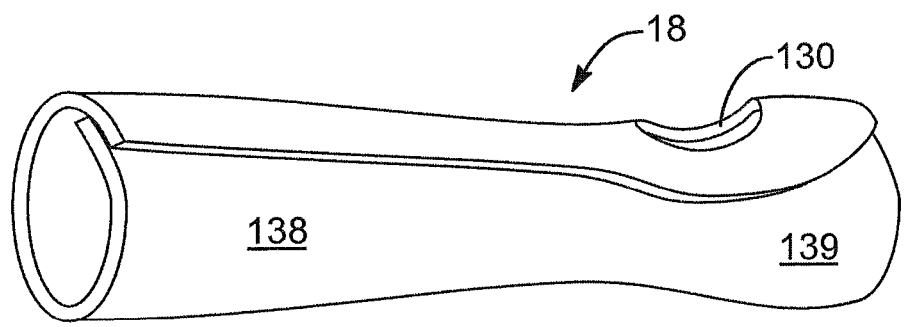
FIG. 44 is a perspective view of one embodiment of a wrist wrap and provided with a penetration for a thumb of a user.
Figure 45:
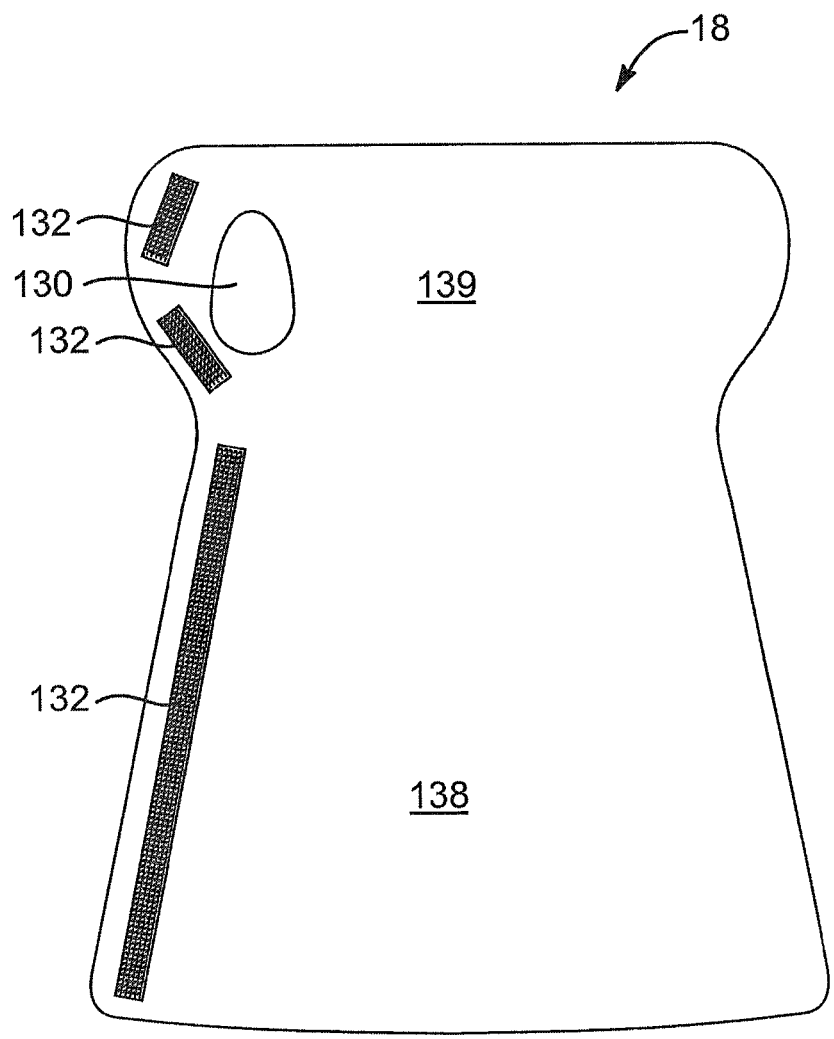
FIG. 45 is a plan view of the wrap of FIG. 44 illustrating the fastener strip and the aperture for a hand.

Referring to FIGS. 44-45, a pad 18 for application to the wrist and hand of a user may include a wrist portion 138 and a hand portion 139. The wrist portion 138 and hand portion 139 may be suitably shaped to wrap around a wrist and hand of a user, relying on a closure 132 or multiple closure sections 132. In certain embodiments, a series of straps, buckles, fasteners, and the like may be used to wrap the pad 18 around a bodily member and fasten to itself or secure it to itself. Nevertheless, in one embodiment, hook-and-loop fasteners may be provided to act as the fastener segments 132. Likewise, an aperture 130 for receiving a thumb therethrough may also be provided as appropriate.

Figure 46:
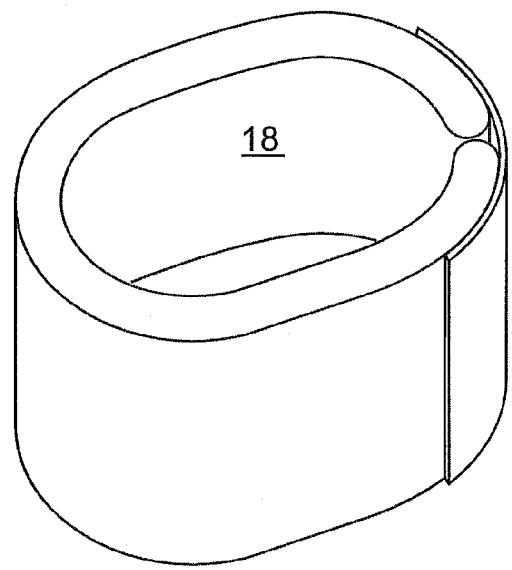
FIG. 46 is a perspective view of one embodiment of a wrap in accordance with the invention suitable for use as a neck collar.
Figure 47:
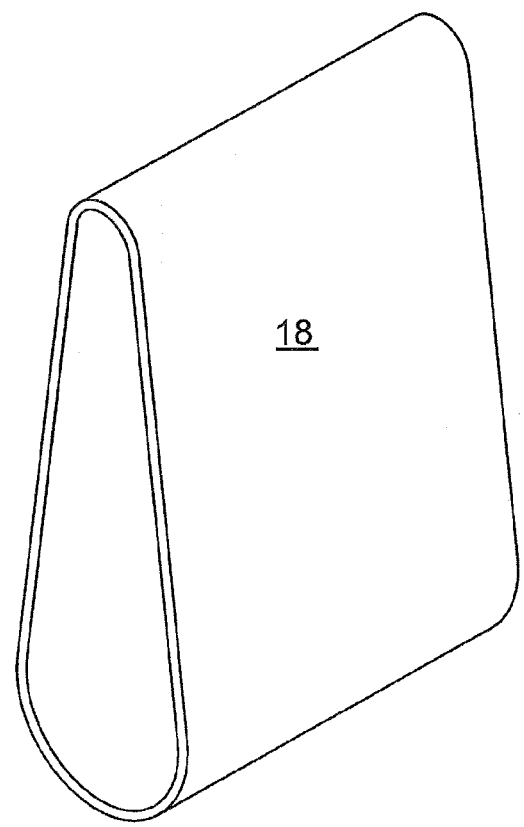
FIG. 47 is a perspective view of wrap in accordance with the invention configured around the outside of a spacing block, such as may be used for maintaining spacing between injured legs.

Referring to FIG. 46, a wrap 18 or pad 18 made in accordance with the invention may be configured in a shape suitable or operating as a collar about a neck of a user. Similarly, a fastener portion 132 may secure the wrap 18 back to itself. Meanwhile, in certain embodiments, pads 18 may be formed in various shapes. For example, in certain embodiments a bodily member may be elevated by a wedge shape, or bodily members may be needing separation from one another. Accordingly, various shapes of pads, pillows, wedges, and the like may be formed in order to position or separate bodily members. Meanwhile, each may be provided as a wrap 18, having a central portion 90 shaped as appropriate in order to provide the suitable sources 20 proximate to members of a recovering user.

Figure 48:
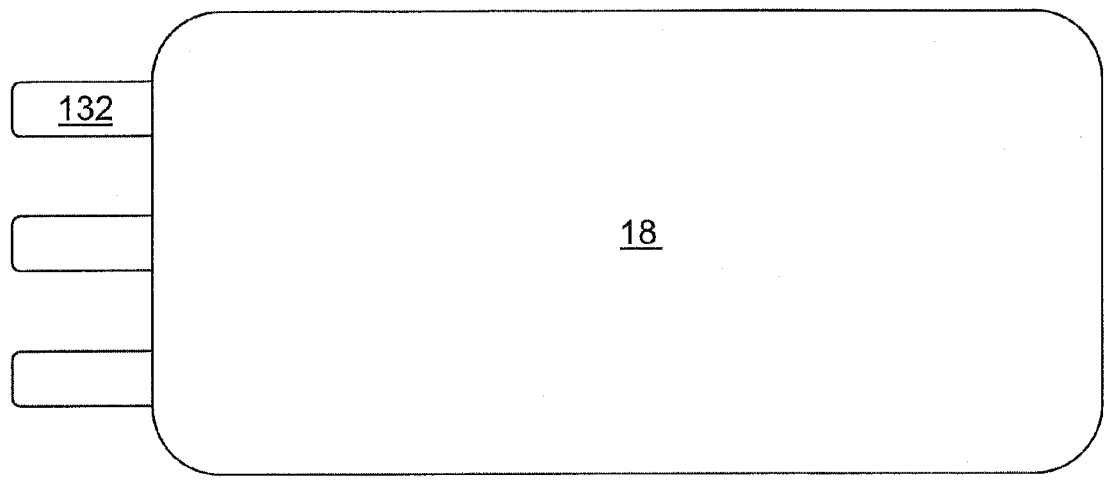
FIG. 48 is a plan view of an alternative embodiment of a wrap in accordance with the invention for wrapping around a member having a substantially constant cross-section.

Referring to FIG. 48, a pad 18 generally may be provided in any suitable shape, including a simple flat shape that may be wrapped around a bodily member at any substantially constant diameter. For example, fasteners 132 may be provided to secure the pad 18 around a member of a user. Similarly, a bodily member such as a forearm, calf, or the like may have a tapered shape requiring a more specific fit. Accordingly, such a shape may be formed as a trapezoid that will wrap to form a somewhat conical wrap 18 or frustum of a cone.

Figure 49:
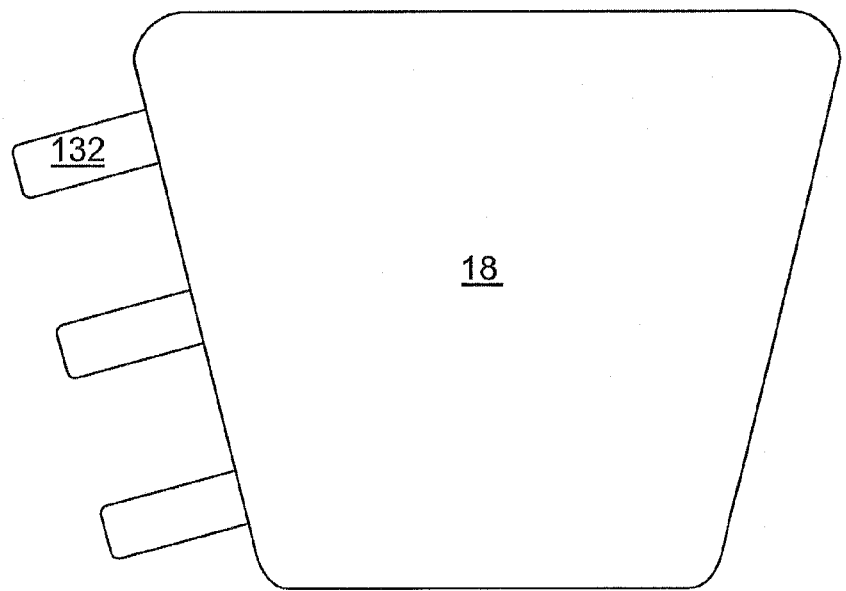
FIG. 49 is a plan view of an alternative embodiment of a wrap in accordance with the invention suitable for wrapping around a tapered member, such as a lower calf, a wrist, or forearm, or the like in which the bodily member has a substantial reduction in cross-section from one end to the other.

Referring to FIG. 49, for example, the pad 18 may be wrapped around a bodily member providing a maximum and minimum diameter when the fasteners 132 secure the pad 18 to itself. Thus, a bodily member having a substantial taper may benefit from the shape of the pad 18 of FIG. 49. Meanwhile, a pad having a rectangular shape, as in FIG. 18, and of suitable length-to-width ratio, may be used about an abdomen, an arm having less dramatic shape change, a collar, or the like.

Figure 50:
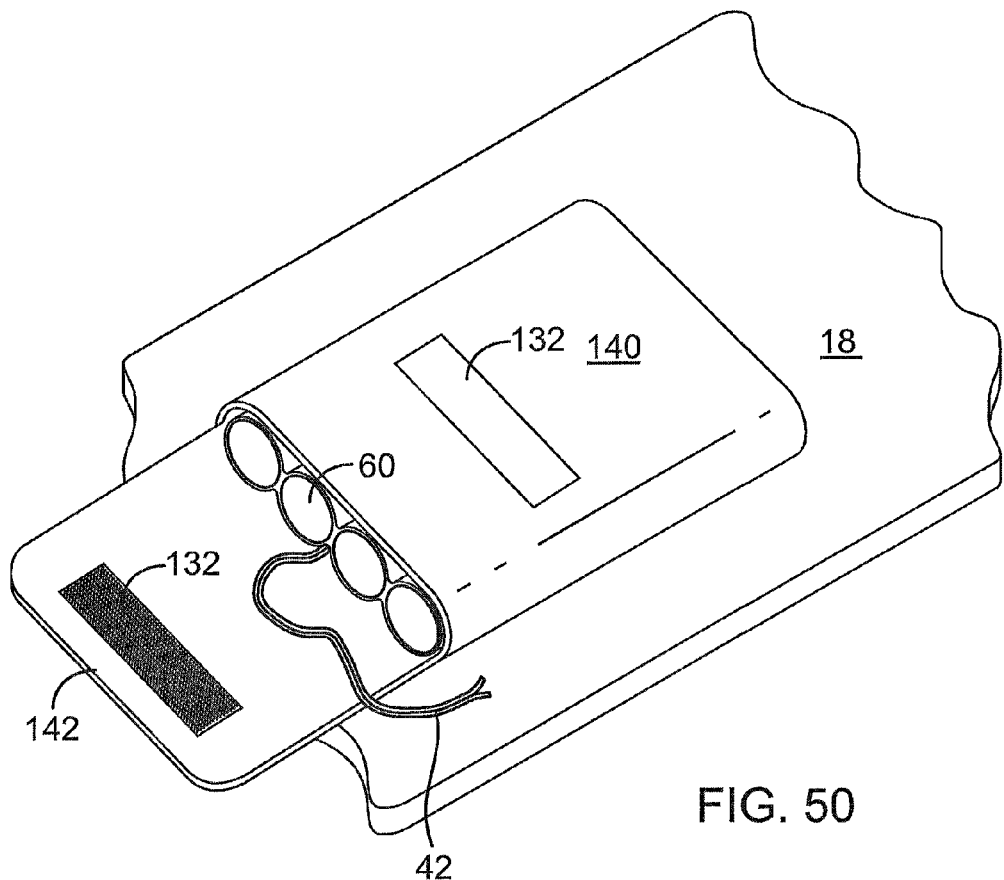
FIG. 50 is a perspective view of one embodiment of an alternative power pack associated with a wrap in accordance with the invention.

Referring to FIG. 50, a pad 18 may include a pocket 140 to hold a controller 22, the power supply 60 or source 60 of power, and the like. In one embodiment, a pocket 140 may be provided a closure 142 secured by fasteners 132. Thus, a set of wires 42 or power lines 142 may proceed from the power supply 60 to a remote controller to magnetic sources 20, or both. For example, the controller may operate in the vicinity or in the same pocket 140 with the power supply 60. Alternatively, the power supply 60 may be provided with wires 42 to a controller remote therefrom.

Figure 51:
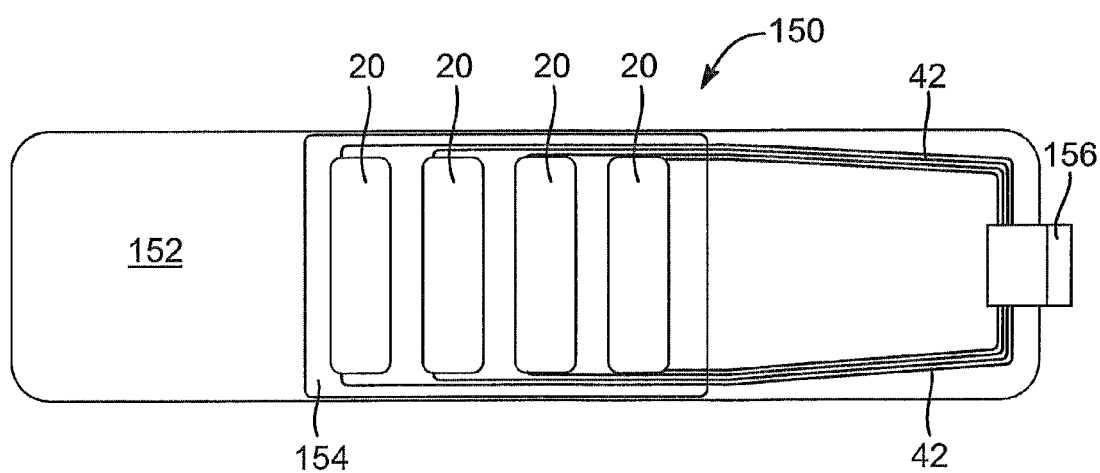
FIG. 51 is a plan view of one embodiment of a dressing having multiple coils provided power through a connector at one end of the dressing.
Figure 52:
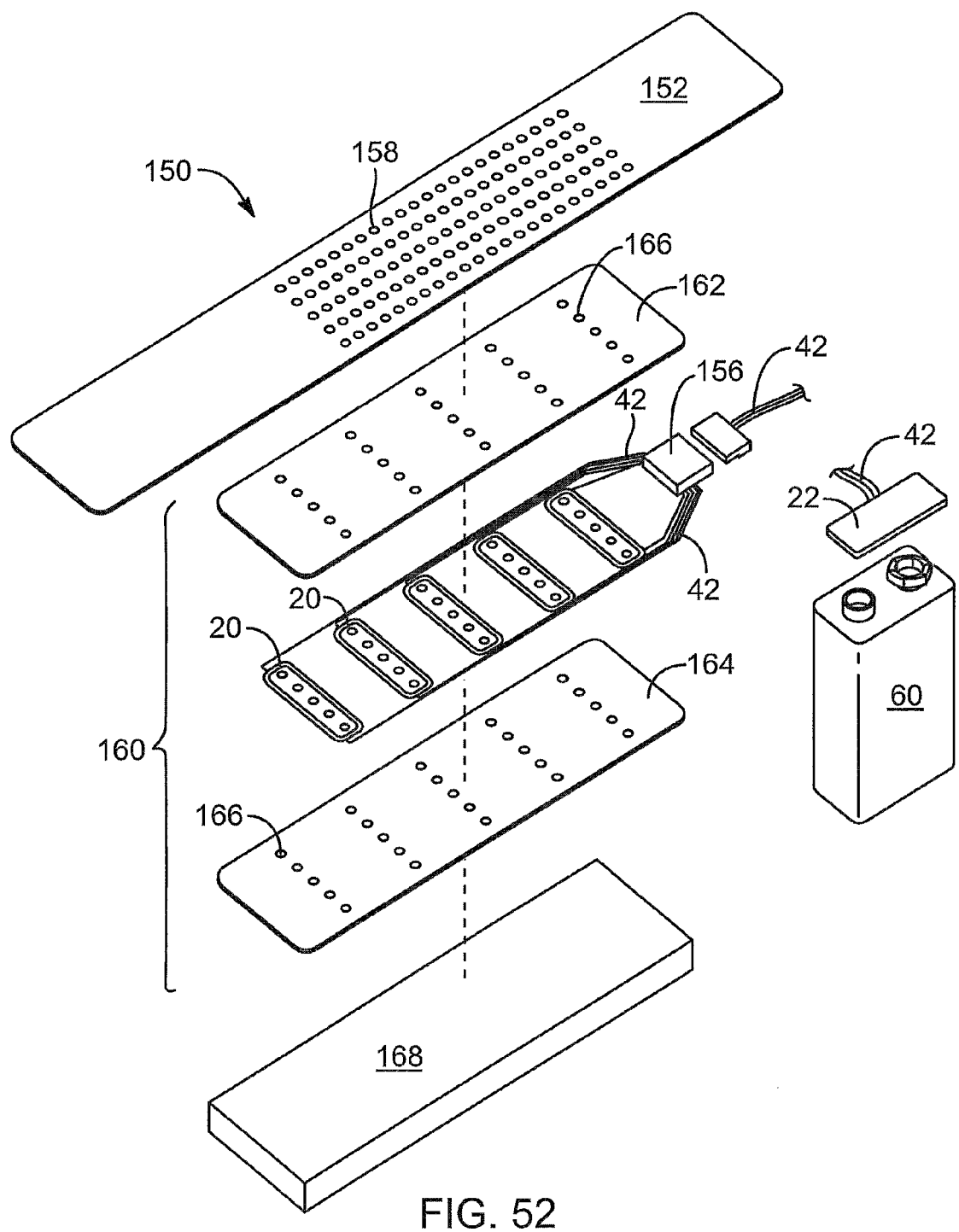
FIG. 52 is an exploded view of a dressing of FIG. 51 illustrating multiple layers for providing the fundamental dressing needs of a wound while applying the electromagnetic coils for remediation of the underlying bone structures, but may be used also to influence the tissue rebuilding, using power from a battery pack such as that of FIG. 50, or the illustrated battery in FIG. 52.
Figure 60:
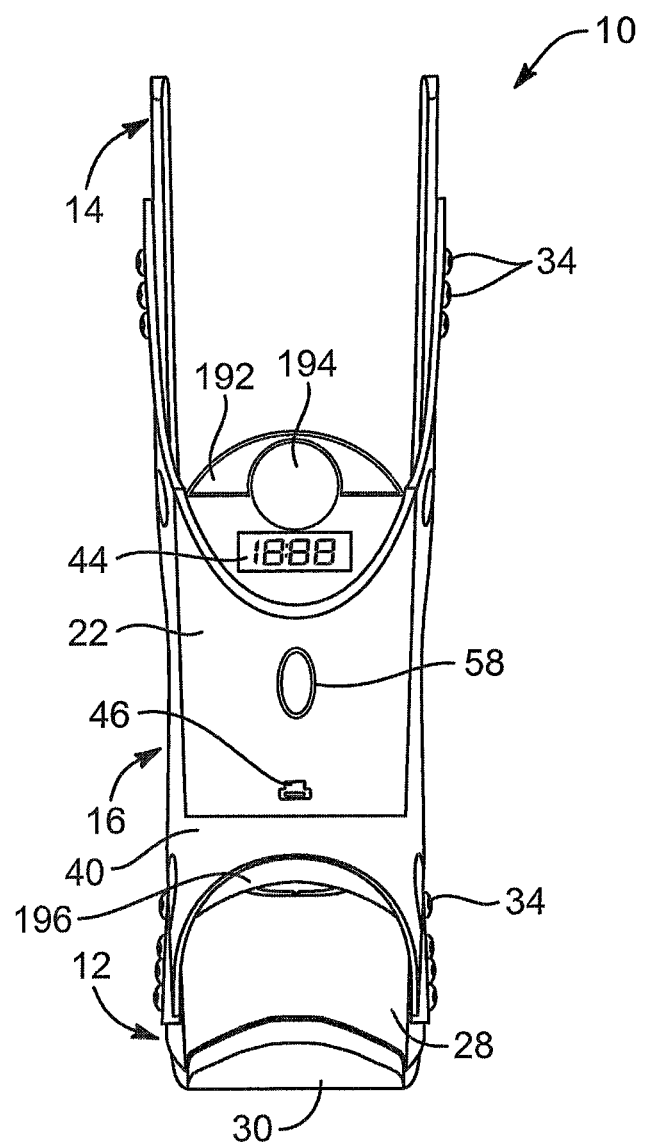
FIG. 60 is a rear elevation view of one embodiment of a removable boot cast in accordance with the invention and providing a gripping loop as part of the structure.
Figure 61:
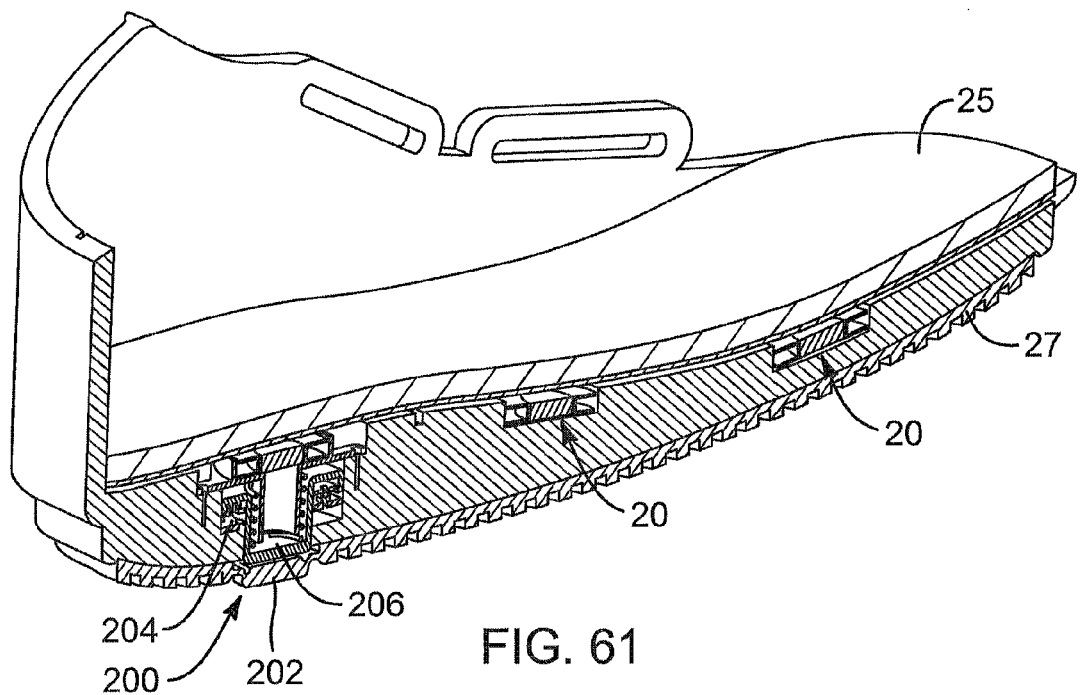
FIG. 61 is a cutaway perspective view of one alternative embodiment of a portion of the frame of a boot cast in accordance with the invention and illustrating a detector to detect motion or force by a wearer, by compromising a witness layer on top or bottom of the foot bed or by a pedometer detecting motion or force.
Figure 62:
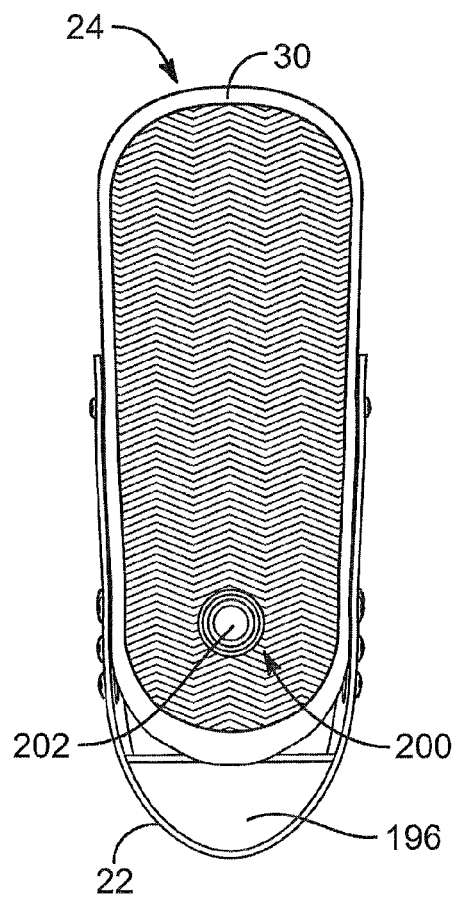
FIG. 62 is a bottom plan view of the apparatus of FIG. 61.

Referring to FIGS. 51-52, for example, the pocket 140 of FIG. 50 may apply to a dressing 150. In the illustrated embodiment, a dressing 150 may include an array of sources 20 containing coils 100, receiving power through a connector 156 on a substrate 152. In certain embodiments, a substrate 152 may provide the structural material establishing a protective cover or the like for a dressing 150. Accordingly, a cover 154 may provide a clear or opaque covering over an array of sources 20 of electromagnetic force or electromagnetic flux. The coils 100 of the sources 20 may connect by wires 42 to a connector 156. The connector 156 may have a mating portion connecting to the wires 42 in a power supply as illustrated in FIG. 60.

In accordance with one embodiment of an apparatus and method in accordance with the invention, the connector 156, may establish separation between a dressing 150, which may need to be changed, and the power supply 60 that may benefit from being used to exhaustion of the available power.

Figure 59:
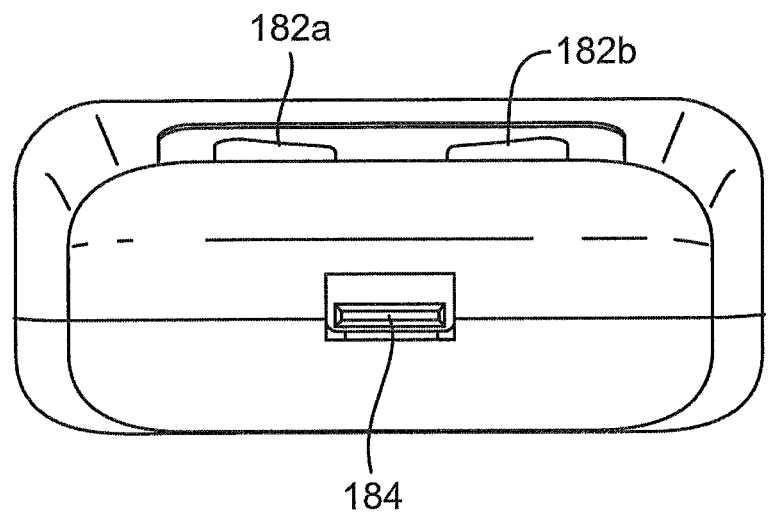
FIG. 59 is an opposite end elevation view of the apparatus of FIG. 54 showing the connection port for connecting to the system of FIG. 53 for programming the controller.

Referring to FIG. 52, while continuing to refer generally to FIGS. 50-52 and while continuing to refer more generally to all FIGS. 1-59, a substrate 152 may include perforations 158. Meanwhile, a connector 156 may be provided as illustrated in detail in FIG. 51. A sealed insert 160 may be provided permitting passage of air or moisture therethrough in accordance with the primary functions of various types of dressings 150.

For example, the perforations 158 may pass through multiple layers including a top layer 162, a bottom layer 164, and the intervening sources 20 with their incorporated coils 100 therein. Thus, the connector 156 may provide access to the outside environment, and connect to the wires 42 of a power supply 60.

The controller 22 may be a simple matter of digital control, or even a matter of on/off control. In certain embodiments, a small oscillator with cycle control may be embedded in the controller 22 secured to the power supply 60 controlling power through the application of voltage, current, or the like as may be selected as the controlled parameter applied to the wires 42.

Meanwhile, wires 42 continue past the connector 156 and on to the sources 20. Meanwhile, the perforations 158 may actually operate as seals, sealing the sources 20 away from any liquids that may be picked up by the gauze 168, filler 168, or other absorber 168 of the dressing. The absorbent material 168 may be any suitable material in one or more layers as contemplated in the medical arts. Thus, the perforations 158 provide access to ambient air for drying of the absorbent material 168. In certain embodiments, the sealed portion 160 may be bonded to the substrate 152, and perforated thereafter, with the perforations 158 aligned with respect to the interior portions of the coils 100 of the sources 20 in particular.

Figure 53:
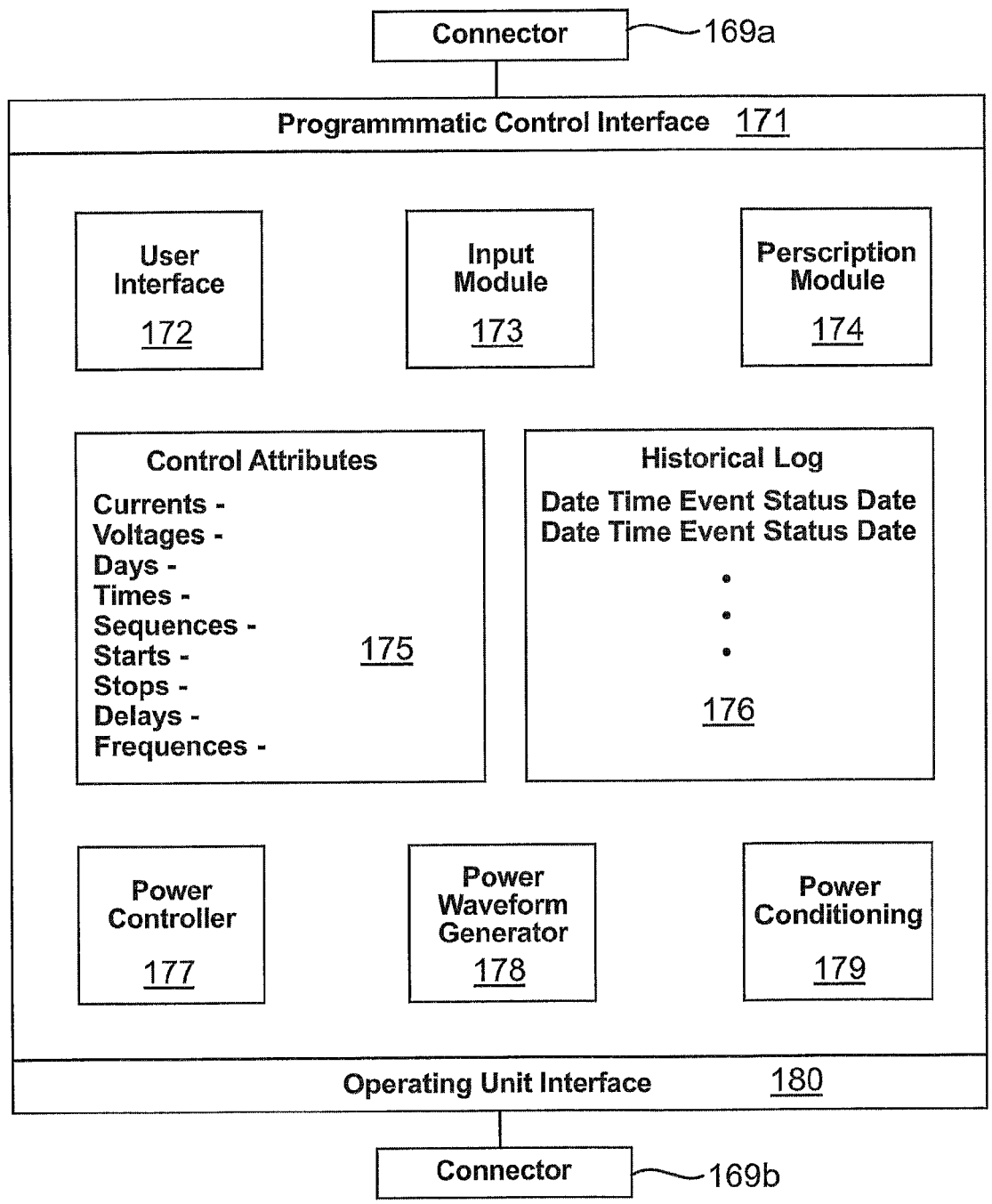
FIG. 53 is a schematic block diagram of one embodiment of a system for providing programmatic control of an apparatus in accordance with the invention, including both a connector for interfacing with a programming system such as a computer or the like, as well as connectors, which are optional, and may be temporary, permanent, or absent for connecting to the unit to be powered and to a source of power.
Figure 54:
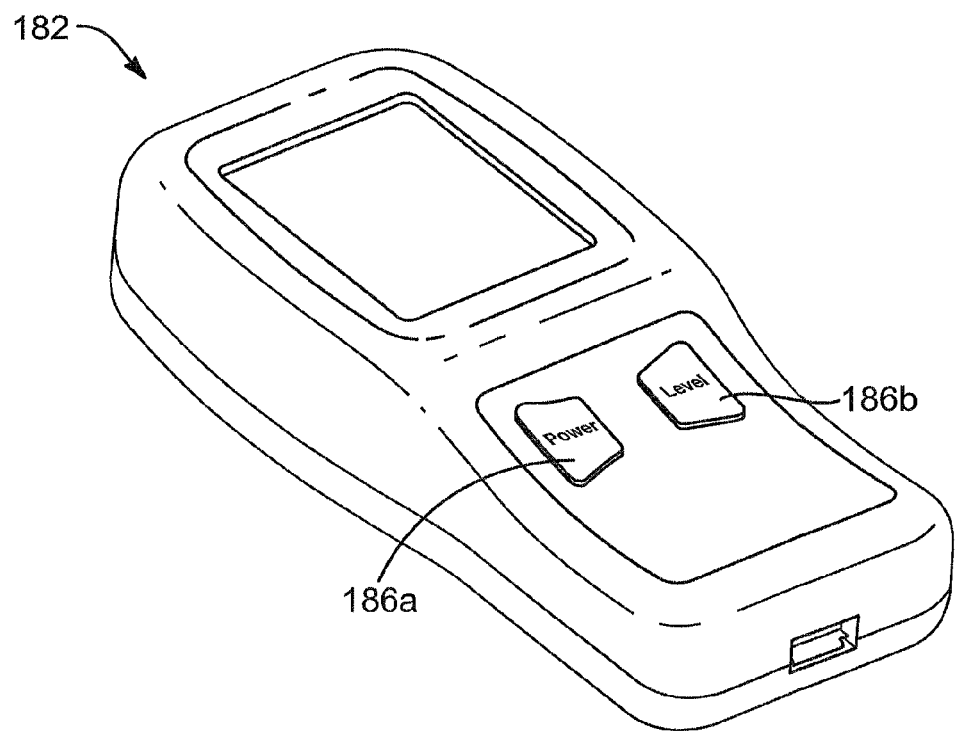
FIG. 54 is a perspective view of one embodiment of a controller for remotely controlling an apparatus in accordance with the invention.
Figure 55:
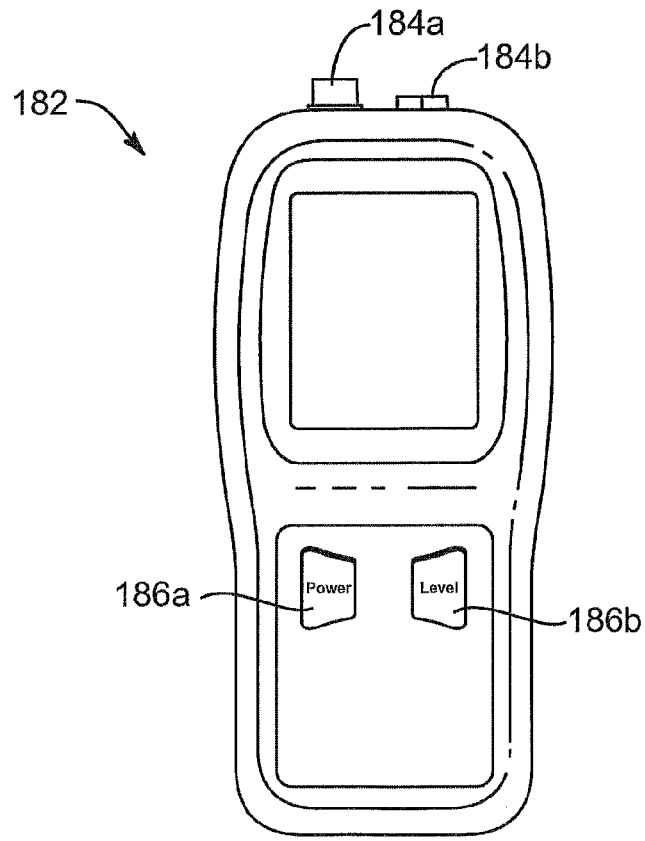
FIG. 55 is a top plan view of the apparatus of FIG. 54.
Figure 56:
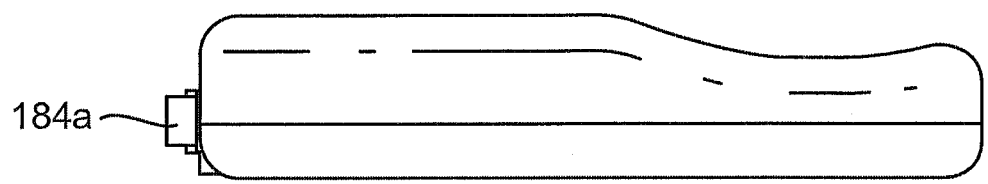
FIG. 56 is a right side elevation view of the apparatus of FIG. 54.
Figure 57:
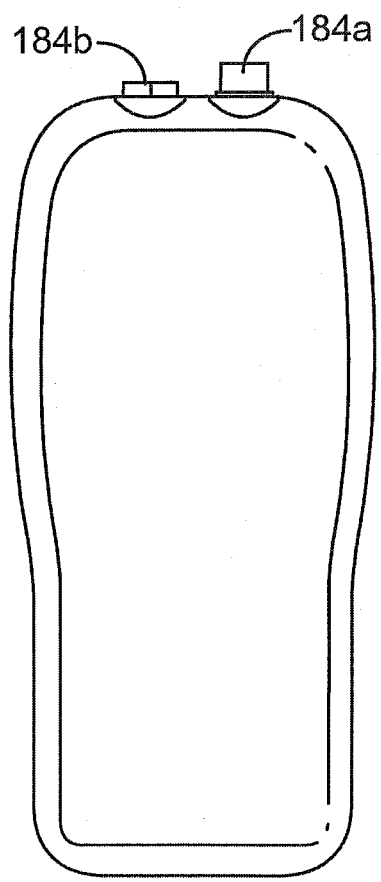
FIG. 57 is a bottom plan view of the apparatus of FIG. 54.
Figure 58:
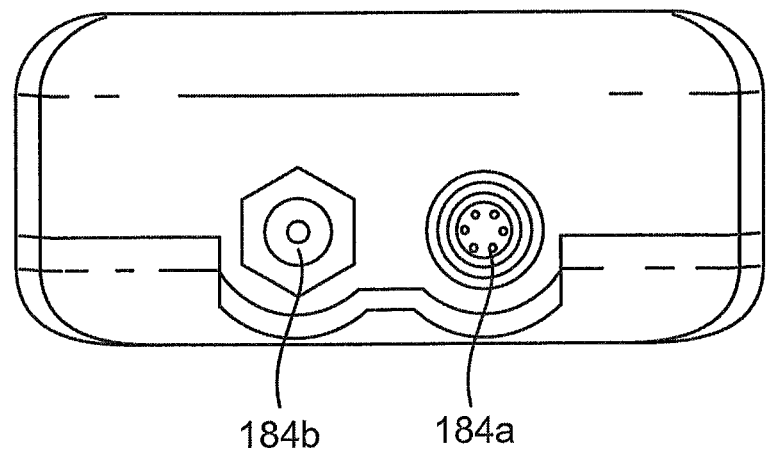
FIG. 58 is an end elevation view of the apparatus of FIG. 54.

Referring to FIG. 53, connectors 169a, 169b may provide an interface between the program system 170 or software system 170 of the apparatus 10. For example, in certain embodiments, the system 170 may actually be embedded in firmware. Regardless of the implementation scheme, the system 170 may connect by the connector 169a to a keyboard, computer, or the like. Accordingly, a programmatic control interface 172 may provide communications to a user through a keyboard, controller, control module, computer, or the like. Thus, an individual user, medical professional, patient, or the like may provide programming into the system 170 through the programmatic control interface 171 upon connection through the connector 169a to a suitable user interface.

Meanwhile, a user interface 172 within the system 170 provides information for operating with some other user input device such as a computer or keyboard, user output device such as a display, or both. Thus, the user interface 172 is responsible to provide queries, prompts, feedback, or the like required to enable and inform a user in programming the system 170. An input module 173 may accept inputs, and provide data exchange with the user interface in order to operate with the hardware and software embedded within the system 170.

In certain embodiments, a prescription module 174 may provide certain standardized regimens. Those regimens may be established by research and medical professionals in order to provide certain standardized, therapeutic formats easily addressed by simple identifiers such as plan numbers. In certain alternative embodiments, the prescription module 174 may interface with a computer of a doctor or other medical professional prescribing a regimen.

Thus, the prescription module 174 may include memory locations for receiving a particular prescription of a user. The prescription module 174 may store a prescription for a cycle description, a time period, or an extended time period with multiple applications throughout multiple days of various regimens.

In certain embodiments, various control attributes 175 may be provided. For example, a system 170 may control current, voltage, or the like. Meanwhile, the system may be programmed to monitor various parameters overtime, such as the current and voltage, and may record them, prescribe them, or the like.

In some embodiments, various days counted from a particular beginning of therapy, days of the week, days of the month, or the like may be provided as control attributes for regimens supplied to a user. Meanwhile, times, including start time, stop time, operation time, duty cycle setting, and the like may be provided. Meanwhile, sequences for sequencing the particular sources 20 that will be operated, or the particular series of coils 100 that will be activated at any time, may be provided.

Startup information may include start times, beginning voltages, wave form shapes, frequencies, and the like controlling the starts. Likewise, stops, including wave form decays, something as simple as wait and start times, or the like may be specified. Delays between cycles, whether those cycles are individual applications of a particular wave form, periods of application of high frequency wave forms, and the like may be provided.

For example, the dwell time between regimen parameters of any type may be specified. The time between application of electromagnetic forces may be very long. For example, in some embodiments, it is contemplated that a regimen may operate for minutes, with multiple starts and stops for short duty cycles within those minutes. Meanwhile, the entire process may then stop for many minutes or even hours. Meanwhile, that regimen within an hour or hours may be repeated within days. Accordingly, all those starts, stops, and delays may be programmed into a regimen.

Likewise, frequencies of oscillation of voltages or other applied power parameters may be specified. Likewise, repetition of cycles may be varied. For example, in some embodiments, a regimen may include application of a particular wave form at a particular voltage for a particular number of cycles, all of which may be changed in subsequent applications within the same regimen. Accordingly, all of those frequencies with their appropriate starts, stops, and delays, may be applied as control attributes.

Typically, feedback is a very important part of medical observation. Accordingly, a historical log 176 may keep track of dates, times, various events, patient status, wave forms, any of the control attributes, and the like.

A power controller 177 may provide the interpreted result of the inputs and control attributes as they will be applied to the actual sources 20. Meanwhile, the power wave form generator 178 may receive or operate to provide the particular voltage or current as a function of time for any particular cycle, for any particular combination of cycles, and for the complete regimen. Thus, the power wave form generator 178 may provide the control information that will control the sources 20 as they receive power from the power controller 177.

Likewise, power conditioning 179 may be required in order to use the apparatus 10 with various sources of power. For example, in certain embodiments, the apparatus may be plugged into a wall outlet and use local line power. In other embodiments, the system 10 may work from batteries 60. Accordingly, the power from the power source 60 whether batteries 60 wall line power 60, or the like may require power conditioning controlled by the power conditioning module 179.

Ultimately, the operating unit interface 180 sends signals to the sources 20 based upon the inputs received, as translated into actual control of the voltage, current, or the like being applied to each particular series in sequence according to the regimen prescribed.

Referring to FIGS. 54-59, an apparatus 10 in accordance with the invention may include a control module 182 operable by a user. In certain embodiments, the control module 182 may be replaced by a computer, a keyboard, or other suitable computer interface appropriate to communicate with the controller 22. In certain embodiments, the control module 182 may be provided with a port 184 suitable for receiving a connection or other interface with the apparatus 10, a programming computer downloading data, both, or the like.

For example, in certain embodiments, the port 184 may actually connect to a flash drive, or USB line, thus connecting the control module 182 to the controller 22 for programming. In certain embodiments, a series of buttons 186 on the control module 182 may provide input by a user of the control inputs for the apparatus 10. In certain embodiments, the button 186a may operate to power the system on or off. Meanwhile, the button 186b may then provide a user with the ability to set the level, to scan through menus on the display 44, or otherwise program or set parameters for the controller 22.

Thus, In certain embodiments, a control module 182 may provide a remote device not requiring any computer, keyboard, or any other interface. For example, if the display 44 of the controller 22 can display menus, cycle through alphanumeric data, or even provide graphical information, then the controller module 182 may provide an interface for a user to program directly the controller 22 according to a desired regimen.

In certain embodiments, of an apparatus and method in accordance with the invention, a user may download applications through the control module 182, and detailed regimens or prescriptions to be loaded into the controller 22.

By the same token, the user may program directly, when convenient, through the port 46 of the controller 22 any desired control information passing into the controller 22. Nevertheless, a benefit of the control module 182 is that a user need not be near a computer in order to operate the system 10 in accordance with the invention.

Connectors 184a, 184b, are optional interfaces for communicating with power supplies, wraps 18, sources 20, or the like. Each is optional and may receive power in, send power out, both, or be absent in any particular embodiment.

Buttons 186 on a control module 182 may be added as convenient for ease of use and understanding by a user. The module 182 may record data such as how often the system 10 is worn, operated, walked on, or the like.

A pedometer may be fitted to the apparatus 10 to detect use, whether proper or improper, by a wearer. Thus, an actuator may move due to contact with a walking surface, thus activating a detector, counter, or the like. The detector may report to the controller 22, control module 182, or the like. Thus a medical professional may obtain a log of proper and improper use by a user.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for micro-exercise of bone mass, the method comprising:

providing a frame-rigid and defining a first space sized to receive a bodily member of a human, the frame comprising a foot bed, extending substantially horizontally, and struts extending vertically up from the foot bed beside the bodily member to leave an opening not less than 180 degrees in a plane orthogonal to the struts, the struts defining a plurality of apertures spaced along the vertical extent thereof;

providing a plurality of coils spaced apart, and each positioned in an aperture of the plurality of apertures and positioned to direct a central axis of electromagnetic flux radially into the bodily member positioned in the first space;

providing a controller fixed to the frame and delivering power to the plurality of coils providing mechanical support to a battery by connecting the battery to the frame in rigid relation thereto;

connecting the battery electrically to the controller to provide power to the controller;

immobilizing the bodily member of a subject within the first space, the bodily member containing a broken bone integral thereto;

programming the controller to provide power to the plurality of coils in a first sequence;

controlling, by the controller, delivery of power to energize the plurality of coils;

delivering to each coil of the plurality of coils power in accordance with the programming of the controller; and delivering, by each coil, an electromagnetic flux into the first space proximate the each coil in accordance with the first sequence; and exercising the cells of the broken bone within the broken bone, in response to the electromagnetic flux while maintaining the broken bone immobile with respect to the first space.

2. The method of claim 1, wherein the frame is at least a portion of at least one of a splint and a cast.

3. The method of claim 2, wherein the cast comprises fasteners rendering the cast selectively removable and re-installable.

4. The method of claim 2, wherein the cast is a boot cast.

5. The method of claim 4, wherein the boot cast further comprises a walking pad.

6. The method of claim 5, wherein the walking pad further comprises a witness element detecting walking.

7. The method of claim 6, wherein the witness element is selected from a destructively modified surface responding to at least one of weighting and wear, a load detector, and a motion detector.

8. The method of claim 7, wherein the witness element is a pedometer.

9. The method of claim 1, further comprising executing a first cycling of the power delivered to the each coil at a first frequency substantially continually during an active portion of a first time period.

10. The method of claim 9, wherein the first frequency is from about 50 to about 500 Hertz.

11. The method of claim 10, wherein the first frequency is selected to be from about 100 to about 300 Hertz.

12. The method of claim 11, wherein the frequency is selected to be from about 150 to about 200 Hertz.

13. The method of claim 9, further comprising executing a first halting of the first cycling for an inactive portion of the first time period.

14. The method of claim 13, further comprising a first repeating of the first cycling and first halting of the first time period throughout a first plurality of time periods, the first plurality of time periods constituting an active portion of a second time period.

15. The method of claim 14, further comprising a second halting of the first repeating for an inactive portion of the second time period.

16. The method of claim 15, further comprising operating the controller to energize the plurality of coils for a total time of the first activated portions of the first cycling for a duty cycle, wherein the duty cycle is the sum of all the active portions of the first cycling occurring during the second time period, divided by the second time period.

17. The method of claim 16, wherein the duty cycle is from about 0.003 to about 0.1.

18. The method of claim 1, further comprising:

separating the coils of the plurality of coils into regions, each region comprising a corresponding, unique, and proper subset of less than all the coils of the plurality of coils; and reducing interference between magnetic fields created by each coil of the plurality of coils by the first sequencing energizing all coils corresponding to each region substantially simultaneously by region and exclusive of all other regions.

19. A method for micro-exercise of bone mass, the method comprising:

providing a frame, selected from a splint and a selectively removable and replaceable cast, the frame being rigid, defining a first space sized to receive a bodily member of a human, and having fasteners rendering the frame selectively removable and re-installable;

the providing the frame, wherein the frame comprises a foot bed extending substantially horizontally in two dimensions and struts extending vertically from the foot bed on opposite sides of the bodily member to leave an opening extending not less than 180 degrees in a horizontal plane orthogonal to the struts, the struts defining a plurality of apertures spaced along the vertical extent thereof;

providing a plurality of coils spaced apart and each positioned in an aperture of the plurality of apertures, and effective to direct the central axis of electromagnetic flux radially into the first space;

providing a controller fixed to the frame and delivering power to the plurality of coils providing mechanical support to a battery by connecting the battery to the frame in rigid relation thereto;

connecting the battery electrically to the controller to provide power to the controller;

immobilizing the bodily member of a subject within the first space, the bodily member containing a broken bone integral thereto;

programming the controller to provide power to the plurality of coils in a first sequence;

controlling, by the controller, delivery of power to energize the plurality of coils;

delivering to each coil of the plurality of coils power in accordance with the programming of the controller; and delivering, by the each coil, an electromagnetic flux into the first space proximate the each coil in accordance with the first sequence; and exercising cells of the broken bone within the broken bone, in response to the electromagnetic flux while maintaining the broken bone immobile with respect to the first space;

the frame further formed to resemble the envelope of a boot, and comprising a witness element selected from a destructively modified surface responding to at least one of weighting and wear, a load detector, and a motion detector;

connecting the coils of the plurality of coils into regions, each region comprising a corresponding, unique, and proper subset of less than all the coils of the plurality of coils;

reducing interference between magnetic fields created by each coil of the plurality of coils by the first sequencing energizing all coils corresponding to each region substantially simultaneously by region and exclusive of all other regions;

executing a first cycling of the power delivered to the each region at a first frequency substantially continually during an active portion of a first time period;

executing a first halting of the first cycling for an inactive portion of the first time period;

executing a first repeating of the first cycling and first halting of the first time period throughout a first plurality of time periods, the first plurality of time periods constituting an active portion of a second time period;

executing a second halting of the first repeating for an inactive portion of the second time period; and operating the controller to energize coils of the plurality of coils for a duty cycle of from about 0.003 to about 0.1, wherein the duty cycle is the sum of all the active portions of the first cycling occurring during the second time period, divided by the second time period.

* * * * *